United States Patent
Yuan et al.

(10) Patent No.: US 11,173,169 B2
(45) Date of Patent: Nov. 16, 2021

(54) SELF-EMULSIFYING FORMULATION OF BISPHOSPHONATES AND ASSOCIATED DOSAGE FORMS

(71) Applicant: Halo Science LLC, Morganville, NJ (US)

(72) Inventors: Xudong Yuan, Morganville, NJ (US); Yu Hui, Winston Salem, NC (US); Tian Zhang, Richmond (CA)

(73) Assignee: Halo Science LLC, Morganville, NJ (US)

( * ) Notice: Subject to any disclaimer, the term of this patent is extended or adjusted under 35 U.S.C. 154(b) by 0 days.

(21) Appl. No.: 15/333,186

(22) Filed: Oct. 25, 2016

(65) Prior Publication Data

US 2018/0110790 A1 Apr. 26, 2018
US 2021/0046095 A9 Feb. 18, 2021

(30) Foreign Application Priority Data

Nov. 1, 2015 (CN) .......................... 201510545906.6

(51) Int. Cl.
| | |
|---|---|
| *A61K 31/675* | (2006.01) |
| *A61K 47/61* | (2017.01) |
| *A61K 47/54* | (2017.01) |
| *A61K 9/00* | (2006.01) |
| *A61K 9/20* | (2006.01) |
| *A61K 9/48* | (2006.01) |
| *A61K 31/59* | (2006.01) |
| *A61K 31/663* | (2006.01) |
| *A61K 45/06* | (2006.01) |

(52) U.S. Cl.
CPC .......... *A61K 31/675* (2013.01); *A61K 9/0095* (2013.01); *A61K 9/2009* (2013.01); *A61K 9/2013* (2013.01); *A61K 9/2018* (2013.01); *A61K 9/2054* (2013.01); *A61K 9/4858* (2013.01); *A61K 9/4866* (2013.01); *A61K 9/4875* (2013.01); *A61K 31/59* (2013.01); *A61K 31/663* (2013.01); *A61K 45/06* (2013.01); *A61K 47/542* (2017.08); *A61K 47/544* (2017.08); *A61K 47/61* (2017.08)

(58) Field of Classification Search
None
See application file for complete search history.

(56) References Cited

U.S. PATENT DOCUMENTS

| | | | |
|---|---|---|---|
| 6,284,268 B1* | 9/2001 | Mishra | A61K 9/1075 424/455 |
| 6,677,320 B2* | 1/2004 | Diederich | A61K 47/183 514/102 |
| 2007/0088161 A1* | 4/2007 | Stockel | C07F 9/58 546/22 |
| 2008/0319056 A1* | 12/2008 | Liu | A61P 7/02 514/470 |

FOREIGN PATENT DOCUMENTS

WO WO-0071163 A1 * 11/2000 ........... A61K 9/0019

OTHER PUBLICATIONS

Tang, Bo, et al. "Development of solid self-emulsifying drug delivery systems: preparation techniques and dosage forms." Drug discovery today 13.13-14 (2008): 606-612.*
Sander, Camilla, and Per Holm. "Porous magnesium aluminometasilicate tablets as carrier of a cyclosporine self-emulsifying formulation." AAPS PharmSciTech 10.4 (2009): 1388.*
Zhang, Yonghui, et al. "Lipophilic bisphosphonates as dual farnesyl/geranylgeranyl diphosphate synthase inhibitors: an X-ray and NMR investigation." Journal of the American Chemical Society 131.14 (2009): 5153-5162.*
Ciosek, C. P., et al. "Lipophilic 1, 1-bisphosphonates are potent squalene synthase inhibitors and orally active cholesterol lowering agents in vivo." Journal of Biological Chemistry 268.33 (1993): 24832-24837.*

* cited by examiner

*Primary Examiner* — John Pak
*Assistant Examiner* — Daniel L Branson
(74) *Attorney, Agent, or Firm* — Seed IP Law Group LLP

(57) ABSTRACT

The patent discloses self-emulsifying formulations of bisphosphonates or bisphosphonic acids in the prevention and treatment of conditions involving calcium or phosphate metabolism. The dosage forms are either capsules, or tablets, or other controlled release drug delivery systems, or devices that contain self-emulsifying formulation of such bisphosphonates or bisphosphonic acids.

14 Claims, 13 Drawing Sheets

SELF-EMULSIFYING FORMULATION OF BISPHOSPHONATES AND ASSOCIATED DOSAGE FORMS

TECHNICAL FIELD

The present invention relates to drug delivery of novel self-emulsifying formulations of bisphosphonates or bisphosphonic acids. The invention additionally relates to dosage forms using the disclosed self-emulsifying drug delivery system.

BACKGROUND

Bisphosphonates or "bisphosphonic acids" are used in the diagnosis and treatment of disorders and conditions related to bone resorption, calcium metabolism and phosphate metabolism, including, but not limited to, osteoporosis, Paget's disease, periprosthetic bone loss or osteolysis, metastatic bone disease, hypercalcemia of malignancy, multiple myeloma, periodontal disease, and tooth loss. These compounds include 1-hydroxyethane-1,1-diphosphonic acid (etidronic acid, salts of which are referred to as "etidronate"), 1,1-dichloromethylene-1,1-bisphosphonic acid (clodronic acid, salts of which are is referred to as "clodronate"), 3-amino-1-hydroxypropylidene-1,1-bisphosphonic acid (pamidronic acid, salts of which are referred to as "pamidronate"), 4-amino-1-hydroxybutylidene-1,1-bisphosphonic acid (alendronic acid, salts of which are referred to as "alendronate), 6-amino-1-hydroxy-hexylidene-1,1-bisphosphonic acid (neridronic acid, salts of which are referred to as "neridronate"), (4-chlorophenyl)-thiomethane-1,1-diphosphonic acid (tiludronic acid, salts of which are referred to as "tiludronate"), 2-(3-pyridinyl)-1-hydroxy-2-(3-pyridinyl)-ethylidene-1,1-bisphosphonic acid (risedronic acid, salts of which are referred to as "residronate"), cycloheptylaminomethylene-1,1-bisphosphonic acid (cimadronic acid, salts of which are referred to as "cimadronate"), 1-hydroxy-3-(N-methyl-N-pentylamino)-propylidene-1,1-bisphosphonic acid (ibandronic acid, salts of which are referred to as "ibandronate"), 3-(dimethylamino)-1-hydroxypropylidene-1,1-bisphosphonic acid (olpadronic acid, salts of which are referred to as "olpadronate"), [2-(2-pyridinyl)-ethylidene]-1,1-bisphosphonic acid (piridronic acid, salts of which are referred to as "piridronate") and 1-hydroxy-2-(1H-imidazol-1-yl)ethylidene-1,1-bisphosphonic acid (zoledronic acid, salts of which are referred to as "zoledronate").

Although the bisphosphonates or bisphosphonic acids are therapeutically effective, oral administration of the drugs is problematic, primarily because of adverse gastrointestinal effects, particularly irritation of the esophagus. Pamidronate has been associated with esophageal ulcers, as has alendronate, although to a lesser extent. Even with risedronate, which can be administered at relatively low doses because of its potency, many patients still complaint heartburn and esophageal burning. Lufkin et al. (1994) Osteoporosis International 4:320-322; De Groen et al. (1996), N. Eng. J. Med. 335(124):1016-1021; Castell et al. (1996) N. Eng. J. Med. 335(124):1058-1059; and Lieberman et al. (1996) N. Eng. J. Med. 3(124):1069-1070. Although efforts have been made to reduce the adverse gastrointestinal effects of the bisphosphonates, there is a continuing need for dosage forms containing these active agents wherein undesirable side effects are minimized and patient compliance and thus therapeutic efficacy are improved.

The bisphosphonates or bisphosphonic acids are highly soluble in water, have a strong polar structure and a strong negative charge at the pH of the small intestine, being also to form insoluble complexes with calcium ions and other bivalent cations in the intestinal lumen. All of these characteristics contribute to the problem of very low oral bioavailability for the bisphosphonates or bisphosphonic acids. In most cases, the bioavailability of the bisphosphonates or bisphosphonic acids is usually less than 1% and highly variable.

The following references pertain to one or more aspects of the invention and may provide useful background information:

U.S. Pat. No. 4,621,077 to Rosini et al. describes biphosphonic acids as therapeutic agents, the acids including alendronate, difluoromethane biphosphonic acid, and 5-amino-1-hydroxypentane-1,1-biphosphonic acid.

U.S. Pat. Nos. 5,358,941 and 5,681,590 to Bechard et al. describe immediate release tablets of bisphosphonic acids and salts thereof, for the treatment of disturbances involving calcium or phosphate metabolism, e.g., treatment and prevention of diseases involving bone resorption, particularly osteoporosis, Paget's disease, malignant hypercalcemia and metastatic bone disease.

U.S. Pat. No. 7,704,977 B2 to Leonard describes oral dosage form of bisphosphonates comprising of a bisphosphonate in combination with an enhancer to enhance intestinal delivery of the bisphosphonate to the underling circulation. The solid oral dosage form is preferably a controlled release dosage form such as a delayed release dosage form.

U.S. Pat. No. 2012/0322767 A1 to Bruzzese describes pharmaceutical formulation of bisphosphonates and vitamin D in high concentration, destined to the intramuscular and subcutaneous intermittent administration for treatment of bone and skeletal system diseases, particularly osteoporosis, and sensitive cancers.

U.S. Pat. No. 2004/0147484 A1 to Boyed and Dinh describes compounds and composition for the delivery of bisphosphonates. These compounds are well suited for forming non-covalent mixtures with bisphosphonates for oral administration to animals.

U.S. Pat. No. 6,372,728 B1 to Ungell describes pharmaceutical formulations of at least one bisphosphonate and an absorption enhancing agent essentially consisting of a medium chain glycerides or a mixture of medium chain glycerides.

U.S. Pat. No. 5,735,810 to Sage and Green describes a method and device for the iontophretic delivery of a therapeutic dose range of bisphosphonate to be delivered to a patient over a period of time to prevent the onset for advancement of osteoporosis and other metabolic bone diseases for a selected period of time.

U.S. Pat. No. 8,535,718 B2 to Dansereau and Burgio describes an oral dosage form comprising of a risedronate and salts thereof; an ethylenediaminetetraacetic acid (EDTA) or a pharmaceutically acceptable salt thereof; and a delayed release mechanism to deliver the risedronate and the EDTA in the lower gastrointestinal tract, wherein the oral dosage form is administered according to a scheduled dosing interval.

U.S. Pat. No. 2006/0210639 A1 to Liversidge and Jenkins describes nanoparticulate bisphosphonate compositions with average particle size of 2000 nm and at least one surface stabilizer. The compositions are useful in treating bone resorption in a mammal.

SUMMARY OF THE INVENTION

Published literature has focused on preparing solid or semi-solid formulations that discharge bisphosphate into digestive tracts directly when mixed with gastric or intestine fluid. No one has reported a self-emulsifying formulation of bisphosphonate complex that undergoes a spontaneous phase transition in contact with gastric or intestinal fluid and thereafter self-emulsification. The phase transition allows the complexed active agent to remain embedded in emulsion vesicles and slowly discharge into bulk medium such as gastric or intestine fluid. Self-emulsifying formulation and controlled release system modify the interaction between active agent and digestive tract, which in turn lessens undesirable irritation as seen in other formulations and potentially improves drug bioavailability.

Accordingly, it is a primary object of the invention to address the above-mentioned need in the art by providing self-emulsifying formulations to potentially improve bioavailability of bisphosphonates or bisphosphonic acid compounds.

It is another object of the invention to provide a dosage form for the administration of bisphosphonates or bisphosphonic acid compounds in self-emulsifying formulations to potentially avoid GI side effects.

It is another object of the invention to provide such a dosage form comprised of a tablet or caplet or film or other solid dosage forms with the drug in a solid carrier.

It is another object of the invention to provide such a dosage form comprised of a capsule, including but not limited to hard capsule or softgel capsule, housing the drug in a solid or liquid or semi-solid carrier.

It is still another object of the invention to provide such a dosage form comprised of a controlled or delayed drug release device.

Additional objects, advantages and novel features of the invention will be set forth in part in the description which follows, and in part will become apparent to those skilled in the art upon examination of the following, or may be learned by practice of the invention.

Generally, the bisphosphonic acid compound has the structure of formula (I)
wherein R1 is selected from the group consisting of hydrido, hydroxyl, alkoxy and halo, and R2 is selected from the group consisting of halo, —(CH2)m-NR3R4, (CH2)n-R5, —O—R6 and —S—R7 wherein m is an integer in the range of zero to 8 inclusive, n is an integer in the range of 1 to 4 inclusive, R3 and R4 are independently hydrido or alkyl, or together form a C5-C7 cyclic group, and R5, R6 and R7 are independently aryl (including heteroaryl) and may be either unsubstituted or substituted with one or more substituents, e.g., halo, particularly chloro. The carrier is a substantially nonaqueous liquid or semi-solid in which the active agent is dissolved or suspended, and may be a solvent, a surfactant, or a combination thereof.

In still another aspect of the invention, a method is provided for treating a patient having a condition that is responsive to administration of an active agent selected from bisphosphonic acids and pharmacologically acceptable bisphosphonate salts, hydrates and other derivatives thereof, the method comprising orally administering to the patient, within the context of an effective dosing regimen, a pharmaceutical formulation as described above, i.e., a tablet, a capsule, an enterically coated capsule, or controlled drug release device. The condition generally involves calcium or phosphate metabolism, i.e., conditions associated with bone resorption such as osteoporosis, Paget's disease, periprosthetic bone loss, osteolysis, malignant hypercalcemia, metastatic bone disease, multiple myeloma, and periodontal disease.

DETAILED DESCRIPTION OF THE INVENTION

I. Definitions and Nomenclature

Figure 1:
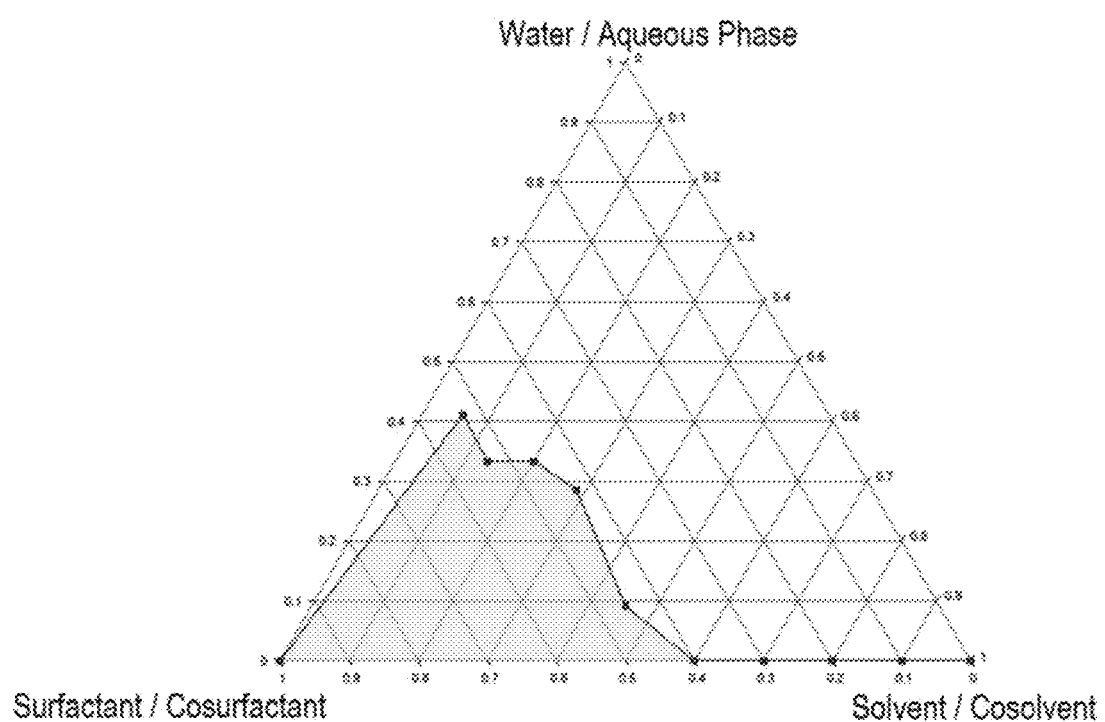
FIG. 1. A typical pseudo ternary phase diagram with three components for a self-emulsifying system FIG. 2. Particle size distribution of the self-emulsifying formulation from Example 1 (The average particle size=88.65 nm)

Before the present formulations and methods of use are disclosed and described, it is to be understood that unless otherwise indicated this invention is not limited to specific pharmacologically active agents, specific pharmaceutical carriers, or to particular administration regimens, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an active agent" includes a single active agent or mixtures of active agents, reference to "a pharmaceutical carrier" includes a single carrier or combinations of two or more carriers, reference to "a coating" refers to a single coating or layers of multiple coatings, and the like.

In this specification and in the claims which follow, reference will be made to a number of terms which shall be defined to have the following meanings:

"Self-emulsifying system" or "self emulsification" in this patent means an emulsion achieved by gentle agitation for the formation of emulsion, instead of traditional high shear homogenization process; the emulsion can be normal emulsion, microemulsion or nanoemulsion.

"Drug delivery system" means approaches, formulations, technologies, and systems for transporting a pharmaceutical compound in the body as needed to safely achieve its desired therapeutic effect.

"Optional" or "optionally" means that the subsequently described circumstance may or may not occur, so that the description includes instances where the circumstance occurs and instances where it does not.

The terms "active agent," "drug" and "pharmacologically active agent" are used interchangeably herein to refer to a chemical material or compound which, when administered to an organism (human or animal, generally human) induces a desired pharmacologic effect. In the context of the present invention, the terms refer to a compound that is capable of being delivered orally.

The term "bisphosphonic acid" or "bisphosphonates" as used herein refers to a compound having the structure of formula (I), below, or to a pharmaceutically acceptable salt, hydrate, ester, anhydride, carbamate, amide thereof.

By the terms "effective amount" or "pharmaceutically effective amount" of an agent as provided herein are meant a nontoxic but sufficient amount of the agent to provide the desired therapeutic effect. As will be pointed out below, the exact amount required will vary from subject to subject, depending on age, general condition of the subject, the severity of the condition being treated, and the particular active agent administered, and the like. An appropriate "effective" amount in any individual case may be determined by one of ordinary skill in the art by reference to the pertinent texts and literature and/or using routine experimentation.

By "pharmaceutically acceptable" carrier is meant a carrier comprised of a material that is not biologically or otherwise undesirable. The term "carrier" is used generically herein to refer to any components present in the pharmaceutical formulations other than the active agent or agents, and thus includes diluents, binders, lubricants, disintegrants, fillers, coloring agents, wetting or emulsifying agents, pH buffering agents, preservatives, and the like.

Similarly, a "pharmaceutically acceptable" salt or a "pharmaceutically acceptable" derivative of a compound as provided herein is a salt or other derivative which is not biologically or otherwise undesirable.

The term "controlled release" is intended to refer to any drug-containing formulation in which the manner and profile of drug release from the formulation are controlled. The term "controlled release" refers to immediate as well as nonimmediate release formulations, with nonimmediate release formulations including but not limited to sustained release and delayed release formulations.

The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between oral administration of the formulation and the release of the drug therefrom. "Delayed release" may or may not involve gradual release of drug over an extended period of time, and thus may or may not be "sustained release." The "delayed release" formulations herein are enterically coated compositions. "Enteric coating" or "enterically coated" as used herein relates to the presence of polymeric materials in a drug formulation that results in an increase in the dosage form's resistance to degradation in the upper gastrointestinal tract, and/or a decrease in the release or exposure of the drug in the upper gastrointestinal tract.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" osteoporosis, as the term "treating" is used herein, encompasses both prevention of osteoporosis in a predisposed individual and treatment of osteoporosis in a clinically symptomatic individual.

The following definitions pertain to chemical structures, molecular segments and substituents:

The term "alkyl" as used herein refers to a branched or unbranched saturated hydrocarbon group of 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkoxy" as used herein intends an alkyl group bound through a single, terminal ether linkage; that is, an "alkoxy" group may be defined as —O-alkyl where alkyl is as defined above. A "lower alkoxy" group intends an alkoxy group containing one to six, more preferably one to four, carbon atoms.

The term "aryl" as used herein, and unless otherwise specified, refers to an aromatic species containing at least 1, and preferably 1 to 5 aromatic rings, either fused or linked, and either unsubstituted or substituted with 1 or more substituents typically selected from the group consisting of lower alkyl, lower alkoxy, halogen, and the like. Heteroatoms may be present, in which case the "aryl" group is "heteroaromatic." Preferred aryl substituents contain 1 aromatic ring or 2 or 3 fused or linked aromatic rings.

The terms "halo" and "halogen" are used in the conventional sense to refer to a chloro, bromo, fluoro or iodo substituent. Preferred halo substituents herein are chloro.

The terms "continuous" or "continuously," as used herein, mean at regular specified intervals. For example, a continuous schedule according to a dosing regimen of once weekly means that the active is given one time per week for an unspecified period of time or for as long as treatment is necessary.

The term "pharmaceutical composition," as used herein, means an oral dosage form comprised of a safe and effective amount of a bisphosphonate active ingredient and one or more pharmaceutically-acceptable excipients to form self-emulsifying formulation. The pharmaceutical compositions described herein are comprised of from 0.05% to 95%, preferably from 1% to 40% of a bisphosphonate active ingredient and from 25% to 99.95%, preferably from 60% to 99% of pharmaceutically-acceptable excipients.

The term "oral dosage form," as used herein, means any pharmaceutical composition intended to be administered to the lower gastrointestinal tract of a human or other mammal via the mouth of said human or other mammal.

The term "unit dose" or "unit dosage" means a dosage form containing an amount of pharmaceutical active or nutrient suitable for administration in one single dose, according to sound medical practice. The present invention is particularly useful for the administration of unit doses in the form of tablets and capsules.

The term "gastrointestinal tract" or "GI tract," as used herein, relates to the alimentary canal, i.e., the musculomembranous tube about thirty feet in length, extending from the mouth to the anus. The term "upper gastrointestinal tract," as used herein, means the buccal cavity, the pharynx, the esophagus, and the stomach. The term "lower gastrointestinal tract," as used herein, means the small intestine and the large intestine.

The term "small intestine," as used herein, means the part of the lower gastrointestinal tract consisting of the duodenum, the jejunum, and the ileum, i.e., that portion of the intestinal tract just distal to the duodenal sphincter of the fundus of the stomach and proximal to the large intestine.

The term "large intestine," as used herein, means the part of the lower gastrointestinal tract just distal to the small intestine, beginning with the cecum, including the ascending colon, the transverse colon, the descending colon, the sigmoid colon, and the rectum.

II. The Novel Formulations

The current invention features pharmaceutical dosage forms that provide for self-emulsifying formulation of a bisphosphonate or bisphosphonic acid compound. Bisphosphonate or bisphosphonic acid compound interacts with various components in emulsion, and therefore forms complex emulsion vesicles. The emulsion vesicles can be more easily uptaken by cells in small intestine; and as a result the bioavailability of bisphosphonate or bisphosphonic acid compound can be improved.

The bisphosphonates or bisphosphonic acid are prepared as self-emulsifying formulation by using appropriate surfactant and solvents. The emulsion can also be solidified by highly porous carrier particles, which are used to prepare into different dosage forms. The dosage forms can be enterically coated (a) capsules housing a bisphosphonic acid or salt or hydrate thereof in a pharmaceutically acceptable solid, liquid, or semi-solid carrier, and (b) controlled release drug delivery devices. The bisphosphonate or bisphosphonic acid compound generally although not necessarily has the structure of formula (I).

Self-emulsifying formulations or drug delivery systems (SEDDS) are mixtures of oils and surfactants, sometimes containing cosolvents, and can be used for the design of formulations in order to improve the oral absorption and bioavailability. This type of formulation emulsifies spontaneously to produce fine oil-in-water emulsions when introduced into an aqueous phase under gentle agitation. SEDDS can be orally administered in soft or hard gelatin capsules and form fine, relatively stable oil-in-water emulsions upon aqueous dilution.

Self-emulsifying formulation can be solidified into differ solid carriers resulting in solid self-emulsifying drug delivery system (S-SEDDS). S-SEDDS can be orally administered in soft or hard gelatin capsules, tablets, caplets, film, strips, wafers, powders, and other solid dosage forms, and form fine, relatively stable oil-in-water emulsion upon aqueous dilution.

Self-emulsifying formulations, including SEDDS and S-SEDDS, spread readily in the gastrointestinal (GI) tract, and the digestive motility of the stomach and the intestine provide the agitation necessary for self-emulsification. These systems advantageously present the drug in dissolved form and the small droplet size provides a large interfacial area for the drug absorption. SEDDS and S-SEDDS can produce emulsions with a droplet size from 100 nm to several microns; while self-microemulsifying drug delivery systems (SMEDDSs) form transparent microemulsions with a droplet size of less than 100 nm or even 50 nm. When compared with sensitive and metastable dispersed emulsions, which are formed by high shear homogenization, SEDDSs are physically stable formulations that are easy to manufacture.

The said bisphosphonic acids include 1-hydroxyethane-1,1-diphosphonic acid (etidronic acid), 1,1-dichloromethylene-1,1-bisphosphonic acid (clodronic acid), 3-amino-1-hydroxypropylidene-1,1-bisphosphonic acid (paamidronic acid), 4-amino-1-hydroxybutylidene-1,1-bisphosphonic acid (alendronic acid), 6-amino-1-hydroxyhexylidene-1,1-bisphosphonic acid (neridronic acid), (4-chlorophenyl)thiomethane-1,1-diphosphonic acid (tiludronic acid), 1-hydroxy-2-(3-pyridinyl)-ethylidene-1,1-bisphosphonic acid (risedronic acid), cycloheptylaminomethylene-1,1-bisphosphonic acid (cimadronic acid), 1-hydroxy-3-(N-methyl-N-pentylamino)propylidene-1,1-bisphosphonic acid (ibandronic acid), 3-(dimethylamino)-1-hydroxypropylidene-1,1-bisphosphonic acid (olpadronic acid), [2-(2-pyridinyl)ethylidene]-1,1-bisphosphonic acid (piridronic acid) and 1-hydroxy-2-(1H-imidazol-1-yl)ethylidene-1,1-bisphosphonic acid (zoledronic acid). Alendronate (4-amino-1-hydroxy-butylidene-1,1-bisphosphonic acid monosodium salt trihydrate), risedronate, tiludronate, and zoledronate are preferred compounds for administration using the present dosage forms.

The bisphosphonate or bisphosphonic acid compound may be in crystalline or amorphous form, and mixtures of bisphosphonate or bisphosphonic acids may be employed. The bisphosphonates are in the form of a pharmaceutically acceptable salt, ester, anhydride, carbamate, amide, hydrate, or other analog, derivative or prodrug, or a combination thereof (e.g., a sodium salt trihydrate, as in alendronate). Salts of the bisphosphonic acid compounds may be obtained commercially or can be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, amino acids, and the like, as well as inorganic acids, e.g., hydrochloric acid, hydrobromic acid, sulfuric acid, nitric acid, phosphoric acid, and the like. Basic salts of acid moieties, e.g., phosphonic acid groups, may be prepared using a pharmaceutically acceptable base. Salts formed with the phosphonic acid group include, but are not limited to, alkali metal salts, alkaline earth metal salts and organic base salts. For example, bases such as sodium hydroxide, potassium hydroxide, ammonium hydroxide, calcium hydroxide, magnesium hydroxide, trimethylamine, lysine, arginine, triethanolamine, and the like, may be used. Preparation of esters involves functionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Anhydrides, carbamates, amides, hydrates, and other analogs, derivatives and prodrugs can be readily prepared as well, using conventional means, and incorporated into the present formulations.

Self-emulsifying formulation of bisphosphonates contains solvent, co-solvent, surfactant, complexing excipient, and/or carrier. The self-emulsifying process is depends on the nature of the solvent-surfactant pair; the surfactant concentration; the temperature at which self-emulsification occurs. A pseudo-ternary phase diagram is commonly used to develop self emulsifying formulations, including water, solvent, surfactant as three contributing factors (FIG. 1).

Self-emulsifying formulation of the bisphosphonate or bisphosphonic acid comprise one or more pharmaceutically acceptable solvents, which are readily available from commercial sources. Examples of specific solvents include, but are not limited to, the following: aceituno oil; almond oil; arachis oil; babassu oil; blackcurrant seed oil; borage oil; buffalo ground oil; candlenut oil; canola oil; castor oil; Chinese vegetable tallow oil; cocoa butter; coconut oil; coffee seed oil; corn oil; cottonseed oil; crambe oil; *cuphea* species oil; evening primrose oil; grapeseed oil; groundnut oil; hemp seed oil; illipe butter; kapok seed oil; linseed oil; menhaden oil; mowrah butter; mustard seed oil; oiticica oil; olive oil; palm oil; palm kernel oil; peanut oil; poppy seed oil; rapeseed oil; rice bran oil; safflower oil; sal fat; sesame oil; shark liver oil; shea nut oil; soybean oil; stillingia oil; sunflower oil; tall oil; tea seed oil; tobacco seed oil; tung oil (China wood oil); ucuhuba oil; vernonia oil; wheat germ oil; hydrogenated castor oil; hydrogenated coconut oil; hydrogenated cottonseed oil; hydrogenated palm oil; hydrogenated soybean oil; hydrogenated vegetable oil; hydrogenated cottonseed and castor oil; partially hydrogenated soybean oil; partially hydrogenated soy and cottonseed oil; glyceryl tributyrate; glyceryl tricaproate; glyceryl tricaprylate; glyceryl tricaprate; glyceryl triundecanoate; glyceryl trilaurate; glyceryl trimyristate; glyceryl tripalmitate; glyceryl tristearate; glyceryl triarchidate; glyceryl trimyristoleate; glyceryl tripalmitoleate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; glyceryl tricaprylate/laurate/stearate; glyceryl 1,2-caprylate-3-linoleate; glyceryl 1,2-caprate-3-stearate; glyceryl 1,2-laurate-3-myristate; glyceryl 1,2-myristate-3-laurate; glyceryl 1,3-palmitate-2-butyrate; glyceryl 1,3-stearate-2-caprate; glyceryl 1,2-linoleate-3-caprylate; glyceryl palmitostearate; and glyceryl behenate.

Fractionated triglycerides, modified triglycerides, synthetic triglycerides, fat-soluble vitamins, and mixtures of oils or triglycerides are also within the scope of the invention. Particularly preferred oils or triglycerides include vegetable oils, fish oils, animal fats, hydrogenated vegetable oils, partially hydrogenated vegetable oils, medium and long-chain triglycerides, structured triglycerides, and vitamin E and vitamin E derivatives such as tocopheryl acetate and tocopheryl acid succinate, and vitamin E analogues such as tocotrienols. Other triglycerides derivatives include Gelucires (Gattefosse), Maisines (Gattefosse), and Imwitors (Hills). Specific examples of these compositions are as follows: Gelucire 44/14 (saturated polyglycolized glycerides); Gelucire 50/13 (saturated polyglycolized glycerides); Gelucire 53/10 (saturated polyglycolized glycerides); Gelucire 33/01 (semi-synthetic triglycerides of C8-C1 saturated fatty acids); Gelucire 39/01 (semi-synthetic glycerides); other Gelucires, such as 37/06, 43/01, 35/10, 37/02, 46/07, 48/09, 50/02, 62/05, etc.; Maisine 35-I (linoleic glycerides); and Imwitor 742 (caprylic/capric glycerides).

Among the above-listed triglycerides (including surfactant compositions having significant triglyceride content), preferred triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially hydrogenated soy and cottonseed oil; glyceryl tricaproate; glyceryl tricaprylate; glyceryl triciaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate. Other preferred triglycerides are saturated polyglycolized glycerides (Gelucire 44/14, Gelucire 50/13 and Gelucire 53/10), linoleic glycerides (Maisine 354), and caprylic/capric glycerides (Imwitor 742).

Self-emulsifying formulation comprises pharmaceutically acceptable solvents or co-solvents. Solvents are generally selected from the following groups: (1) aqueous media, including water and aqueous buffers; (2) alcohols and polyols, such as ethanol, isopropanol, butanol, benzyl alcohol, ethylene glycol, propylene glycol, butanediols and isomers thereof, glycerol, pentaerythritol, sorbitol, mannitol, diethylene glycol monoethyl ether, diethylene glycol monomethyl ether, dimethyl isosorbide, polyethylene glycol (PEG), polypropylene glycol, polyvinylalcohol, hydroxypropyl methylcellulose and other cellulose derivatives, cyclodextrins and cyclodextrin derivatives such as hydroxypropyl cyclodextrins; (3) ethers, such as dimethyl isosorbide, and ethers of polyethylene glycols having an average molecular weight of about 200 to about 6000, such as tetrahydrofurfuryl alcohol PEG ether or methoxy PEG; (4) amides such as 2-pyrrolidone, 2-piperidone, caprolactam, N-alkyl-pyrrolidones (e.g., N-methylpyrrolidone), N-hydroxyalkyl-pyrrolidone (e.g., N-hydroxyethylpyrrolidone), N-alkylpiperidones, N-alkylcaprolactams, dimethylacetamide, and polyvinylpyrrolidone; and (5) esters such as ethyl propionate, tributylcitrate, acetyl triethylcitrate, acetyl tributylcitrate, triethylcitrate, ethyl oleate, ethyl caprylate, ethyl butyrate, triacetin, monooctanoin, propylene glycol monoacetate, propylene glycol diacetate, caprolactone and isomers thereof, valerolactone and isomers thereof, and butyrolactone and isomers thereof.

Self-emulsifying formulation also comprise pharmaceutically acceptable surfactants or co-surfactants. The surfactants or co-surfactants may be hydrophilic or lipophilic. As is well known in the art, the terms "hydrophilic" and "lipophilic" or "hydrophobic" are relative terms. To function as a surfactant, a compound must necessarily include polar or charged hydrophilic moieties as well as non-polar lipophilic (hydrophobic) moieties; that is, a surfactant compound must be amphiphilic. An empirical parameter commonly used to characterize the relative hydrophilicity and hydrophobicity of non-ionic amphiphilic compounds is the hydrophilic-lipophilic balance ("HLB" value). Suitable hydrophilic surfactants for use in the present formulations are any hydrophilic surfactants that are acceptable for use in pharmaceutical compositions. Such surfactants can be anionic, cationic, zwitterionic or non-ionic. These non-ionic hydrophilic surfactants will generally have HLB values greater than about 10. Mixtures of hydrophilic surfactants are also within the scope of the invention. Similarly, suitable lipophilic surfactants for use in the present formulations are any lipophilic surfactants that are acceptable for use in pharmaceutical compositions. In general, suitable lipophilic surfactants will have an HLB value less than about 10. Mixtures of lipophilic surfactants are also within the scope of the invention.

Surfactants useful herein include, but are not limited to, polyethylene glycol fatty acid esters, alcohol-oil transesterification products, polyglycerized fatty acids, propylene glycol fatty acid esters, mixtures of propylene glycol fatty acid esters and glycerol fatty acid esters, mono- and diglycerides, sterol and sterol derivatives, sorbitan fatty acid esters and polyethylene glycol sorbitan fatty acid esters, sugar esters, polyethylene glycol alkyl ethers and polyethylene glycol alkyl phenol ethers, polyoxyethylene-polyoxypropylene block copolymers, lower alcohol fatty acid esters, ionic surfactants, and ionizable surfactants, as follows.

Polyethylene Glycol Fatty Acid Esters: Although polyethylene glycol itself does not function as a surfactant, a variety of PEG-fatty acid esters, such as PEG-fatty acid monoester, PEG-fatty acid diesters, and PEG-fatty acid mono- and di-ester mixtures have useful surfactant properties. Among the PEG-fatty acid esters, esters of caproic acid, caprylic acid, capric acid, lauric acid, oleic acid, stearic acid, linoleic acid, and linolenic acid are especially useful.

Alcohol-Oil Transesterification Products: A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, maltol, sorbitol, and pentaerythritol. Among these alcohol-oil transesterified surfactants, preferred hydrophilic surfactants are PEG-35 castor oil, PEG-40 hydrogenated castor oil, PEG-25 trioleate, PEG-60 corn glycerides, PEG-60 almond oil, PEG-40 palm kernel oil, PEG-50 castor oil, PEG-50 hydrogenated castor oil, PEG-8 caprylic/capric glycerides, and PEG-6 caprylic/capric glycerides. Preferred lipophilic surfactants in this class include PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, PEG-6 palm kernel oil, PEG-6 triolein, PEG-8 corn oil, PEG-20 corn glycerides, and PEG-20 almond glycerides. The latter two surfactants are reported to have HLB values of ~10, which is generally considered to be the approximate border line between hydrophilic and hydrophobic surfactants. For purposes of the present invention, these two surfactants are considered to be hydrophobic. Also include as oils in this category of surfactants are oil-soluble vitamins, such as vitamins A, D, E, K, and their analogues and derivatives, etc. Thus, derivatives of these vitamins, such as tocopheryl PEG-1000 succinate, are also suitable surfactants.

Polyglycerized Fatty Acids: Among the polyglyceryl fatty acid esters, preferred hydrophilic surfactants include polyglyceryl-10 laurate, polyglyceryl-10 oleate, and polyglyceryl-10 mono, dioleate. Preferred lipophilic surfactants include polyglyceryl oleate, polyglyceryl-2 dioleate, and polyglyceryl-10 trioleate. Polyglyceryl polyricinoleates are also preferred hydrophilic and lipophilic surfactants.

Propylene Glycol Fatty Acid Esters: Both mono- and diesters of propylene glycol may be used. In this surfactant class, preferred lipophilic surfactants include Capryol 90, Labrafac PG, propylene glycol monolaurate, propylene glycol ricinoleate, propylene glycol monooleate, propylene glycol dicaprylate/dicaprate, and propylene glycol dioctanoate.

Mixtures of Propylene Glycol Fatty Acid Esters and Glycerol Fatty Acid Esters: In general, mixtures of surfactants are also suitable for use in the present invention. In particular, mixtures of propylene glycol fatty acid esters and glycerol fatty acid esters are suitable and are commercially available. One preferred mixture is composed of the oleic acid esters of propylene glycol and glycerol.

Mono- and Diglycerides: A particularly important class of surfactants are the mono- and diglycerides. These surfactants are generally lipophilic. Preferred lipophilic surfactants in this class of compounds include glyceryl monooleate, glyceryl ricinoleate, glyceryl laurate, glyceryl dilaurate, glyceryl dioleate, glyceryl mono/dioleate, glyceryl caprylate/caprate, caprylic acid mono/diglycerides, and mono- and diacetylated monoglycerides.

Sterol and Sterol Derivatives: Sterols and derivatives of sterols are can be hydrophilic or hydrophobic. Preferred derivatives include polyethylene glycol derivatives, and a preferred hydrophobic surfactant in this class is cholesterol. Preferred hydrophilic surfactants in this class are PEG-24 cholesterol ether, PEG-30 cholestanol, and phytosterol.

Sorbitan Fatty Acid Esters and Polyethylene Glycol Sorbitan Fatty Acid Esters: A variety of sorbitan esters of fatty acids are suitable surfactants for use in the present invention. Among these esters, preferred hydrophilic surfactants include PEG-sorbitan fatty acid esters, such as PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80). Among these esters, preferred lipophilic surfactants include sorbitan fatty acid esters and some polyethylene glycol sorbitan fatty acid esters, such as sorbitan monolaurate (Arlacel 20), sorbitan monopalmitate (Span-40), sorbitan monooleate (Span-80), sorbitan monostearate, and sorbitan tristearate.

Sugar Esters: Preferred hydrophilic or lipophilic surfactants in this class include sucrose monolaurate, sucrose monopalmitate, sucrose distearate/monostearate, and sucrose acetate isobutyrate.

Polyethylene Glycol Alkyl Ethers and Polyethylene Glycol Alkyl Phenol Ethers: Ethers of polyethylene glycol and alkyl alcohols or phenols are also suitable surfactants for use in the present invention. Preferred ethers include PEG-3 oleyl ether (Volpo 3), PEG-4 lauryl ether (Brij 30), and PEG-10-100 nonyl phenol.

Polyoxyethylene-Polyoxypropylene ("POE-POP") Block Copolymers: The POE-POP block copolymers are a unique class of polymeric surfactants. The unique structure of the surfactants, with hydrophilic POE and hydrophobic POP moieties in well-defined ratios and positions, provides a wide variety of surfactants that are suitable herein. These surfactants are available under various trade names, including Synperonic PE series (ICI); Pluronic, Emkalyx, Lutrol (BASF), Supronic, Monolan, Pluracare, and Plurodac. The generic term for these polymers is "poloxamer" (CAS 9003-11-6). These polymers have the formula HO(C2H4O)a(C3H6O)b(C2H4O)aH where "a" and "b" denote the number of polyoxyethylene and polyoxypropylene units, respectively. Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Lower Alcohol Fatty Acid Esters: Esters of lower alcohols (C2 to C4) and fatty acids (C8 to C18) are suitable surfactants for use in the present formulations. Among these esters, preferred hydrophobic surfactants include ethyl oleate, isopropyl myristate, and isopropyl palmitate.

Ionic Surfactants: Ionic surfactants, including cationic, anionic and zwitterionic surfactants, may also be used. Preferred ionic surfactants include fatty acid salts, bile salts, phospholipids, carnitines, ether carboxylates, succinylated monoglycerides, mono/diacetylated tartaric acid esters of mono- and diglycerides, citric acid esters of mono-, diglycerides, alginate salts, and lactylic esters of fatty acids. Specifically, preferred ionic surfactants include sodium oleate, sodium lauryl sulfate, sodium lauryl sarcosinate, sodium dioctyl sulfosuccinate, sodium cholate, sodium taurocholate, lauroyl carnitine; palmitoyl carnitine; and myristoyl carnitine. It will be appreciated by one skilled in the art, however, that any bioacceptable counterion may be used. For example, although the fatty acids are shown as sodium salts, other cation counterions can also be used, such as alkali metal cations or ammonium. In contrast to typical non-ionic surfactants, these ionic surfactants are generally available as pure compounds.

Ionizable Surfactants: Ionizable surfactants, when present in neutral, uncharged form, are lipophilic (hydrophobic) surfactants suitable for use in the compositions and methods of the present invention, and in their ionized form, are hydrophilic surfactants suitable for use in the present invention. Particular examples of such surfactants include free fatty acids, particularly C6-C22 fatty acids, and bile acids. More specifically, suitable unionized ionizable surfactants include the free fatty acid and bile acid forms of any of the fatty acid salts and bile salts. Preferred ionizable surfactants include fatty acids and their corresponding salts, such as caprylic acid/sodium caprylate, oleic acid/sodium oleate, capric acid/sodium caprate; ricinoleic acid/sodium ricinoleate, linoleic acid/sodium linoleate, and lauric acid/sodium laurate; trihydroxy bile acids and their salts, such as cholic acid (natural), glycocholic acid and taurocholic acid; dihydroxy bile acids and their salts, such as deoxycholic acid (natural), glycodeoxycholic acid, taurodeoxycholic acid, chenodeoxycholic acid (natural), glycochenodeoxycholic acid, taurochenodeoxycholic acid, ursodeoxycholic acid, tauroursodeoxycholic acid, and glycoursodeoxycholic acid; monohydroxy bile acids and their salts, such as lithocholic acid (natural); sulfated bile salt derivatives; sarchocholate; fusidic acid and its derivatives; phospholipids, such as phosphatidyl choline, phosphatidyl ethanolamine, phosphatidyl serine, PD inositol, lecithin, lysolecithin, and palmitoyl lysophosphatidyl choline; carnitines, such as palmitoyl carnitine, lauroyl carnitine and myristoyl carnitine; chitosan and derivatives, long carbon chain tertiary or quaternary ammonium, cyclodextrins, including alpha, beta and gamma cyclodextrins; and modified cyclodextrins, such as hydroxy propyl and sulfobutyl ether.

Complexing excipients: complexing agents include cationic, zwitterionic lipids or polymers or other positively charged agents to form complex with negatively charged bisphosphonates or bisphosphonic acids. Complex of bisphosphonates assists the actives to be embedded or absorbed to the lipophilic phase in the phase transition process, and therefore improve the absorption in GI and the bioavailability as a result.

The solid carrier can be used to solidify the emulsion and forms solid self-emulsifying drug delivery system (S-SEDDS) or formulation. Ideally, the solid carriers are porous with large surface area. The solid carriers include but not limited to: dibasic calcium phosphonate, magnesium aluminometasilicate, lactose, methyl cellulose, HPMC and other cellulose derivatives, magnesium stearate, croscarmellose sodium, silica dioxide, calcium carbonate, starch, dextrin, maltodextrin, cyclodextrin, dextran, silicate, zinc dioxide, and other solid carriers.

In addition to the carrier, the drug-containing formulation of the invention can further include pharmaceutically acceptable excipients or additives. Such additives include buffering agents, pH adjusters, polymers, antioxidants, preservatives, chelating agents, viscomodulators, tonicifiers, flavorants, colorants odorants, opacifiers, suspending agents, anti-foaming agents, binders, fillers, plasticizers, lubricants, and mixtures thereof. The amounts of such additives can be readily determined by one skilled in the art, according to the particular properties desired.

One or more additional active agents can also be included in the dosage forms in order to potentiate certain effects of the bisphosphonic acid, or can alleviate side effects associated with bisphosphonic acid administration, particularly esophageal irritation. Each of the additional active agents, like the bisphosphonic acid, may be in the form of a pharmaceutically acceptable salt, ester, amide, or other analog, derivative or prodrug, including active agents modified by appending one or more appropriate functionalities to enhance selected biological properties.

Self-emulsifying formulation can also be used as an emulsion or suspension with other excipients and are filled into hard capsules with seals or softgel capsules, such as gelatin, starch, cellulosic, and HPMC capsules. The solidified self-emulsifying powders can be further mixed with other excipients, such as diluents, binders, fillers, lubricants, colorants, and compressed as tablets or caplets. The powder can also be filled into capsules, used for film, strip, sachet, or other solid dosage forms. Tablets and capsules can be further coated with enteric coating polymers or other materials to obtain enteric coated formulations in order deliver the drugs directly to small intestine and avoid gastric irritation and side effects in upper GI tract. Enteric coating materials include, but are not limited to: cellulosic polymers, acrylic acid polymers and copolymers, vinyl polymers and copolymers, and shellac. Combinations of different coating materials may also be used to coat a single capsule.

III. Utility

The novel drug dosage forms are to be administered orally to a mammalian individual and can be used to administer a bisphosphonic acid or bisphosphonate compound as an active agent with improved bioavailability and reduced side effects. In accordance with the present invention, administration of a bisphosphonic acid compound or bisphosphonate may be carried out in order to treat any disorder, condition or disease for which such a compound is generally indicated. Such disorders, conditions and diseases include, for example, disturbances involving calcium or phosphate metabolism, e.g., involving bone resorption, particularly osteoporosis, Paget's disease, periprosthetic bone loss or osteolysis, malignant hypercalcemia, metastatic bone disease, multiple myeloma, cancer, periodontal disease, and tooth loss. Dosage regimens and daily dosage for bisphosphonic acid or bisphosphonate compounds can vary due to different bisphosphonate drugs and different patient's conditions.

EXAMPLES

The practice of the present invention will employ, unless otherwise indicated, conventional techniques of pharmaceutical formulation, medicinal chemistry, biological testing, and the like, which are within the skill of the art. Such techniques are explained fully in the literature. Preparation of various types of pharmaceutical formulations are described, for example, in Lieberman et al., cited supra; and Gibaldi and Perrier, Pharmacokinetics (Marcel Dekker, 1982), provides a description of the testing procedures useful to evaluate drug delivery systems described and claimed herein.

Example 1

Figure 2:
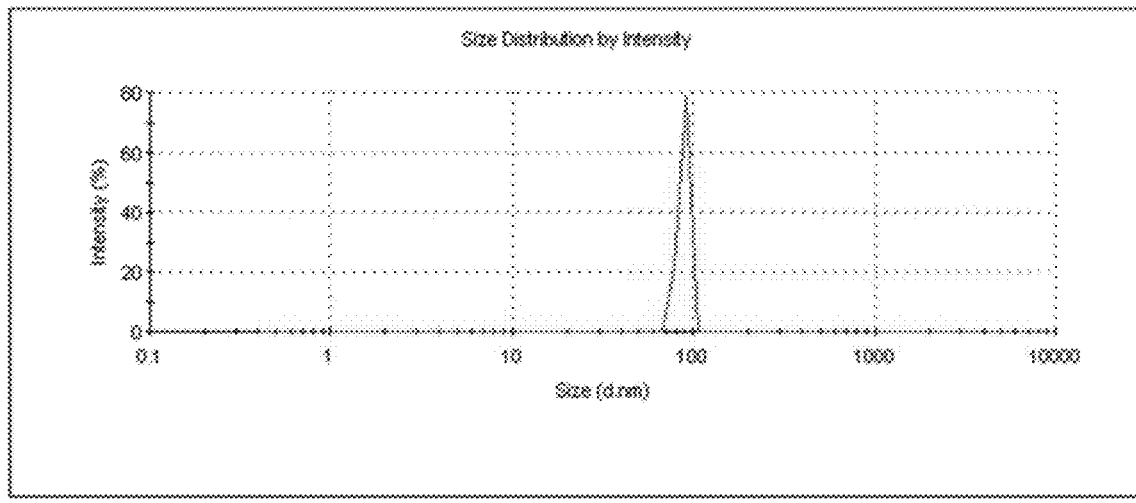

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The obtained self-emulsifying preparation was characterized for the particle size by a Malvern dynamic laser diffraction particle size analyzer (FIG. 2).

| Ingredient | Quantity | Function |
|---|---|---|
| Alendronate | 1 g | API |
| PEG 400 | 20 g | Solvent |
| Benzyl alcohol | 17 g | Co-solvent |
| Span 80 | 25 g | Surfactant |
| Lecithin | 2 g | Co-surfactant/Complexing Excipient |
| Purified water | 100 g | Co-solvent |

Example 2

Figure 3:
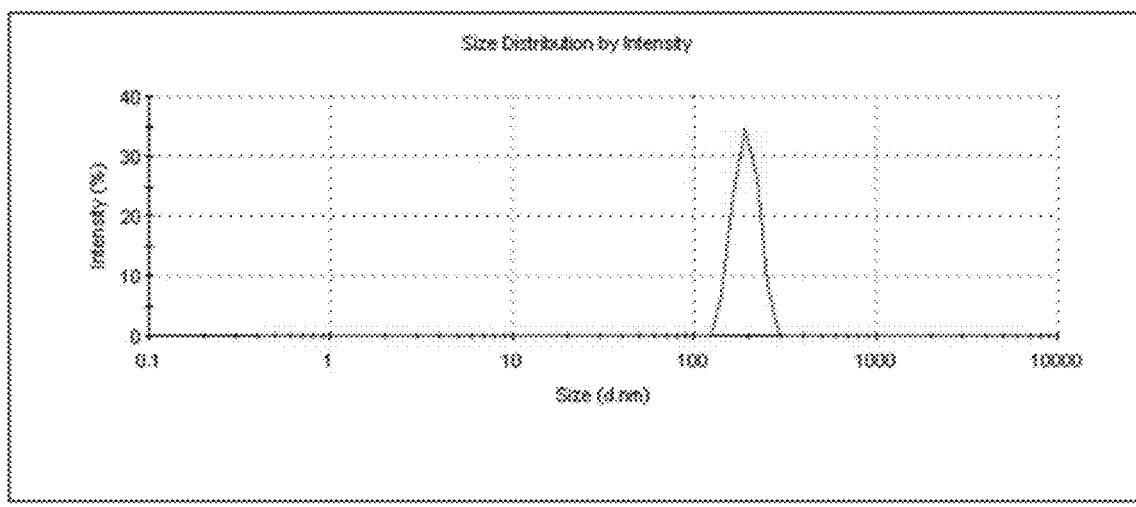
FIG. 3. Particle size distribution of the self-emulsifying formulation from Example 2 (The average particle size=194.4 nm)

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The obtained self-emulsifying preparation was characterized for the particle size by a Malvern dynamic laser diffraction particle size analyzer (FIG. 3).

| Ingredient | Quantity | Function |
|---|---|---|
| Alendronate | 1 g | API |
| Miglyol 812 | 95 g | Solvent |
| Tween 80 | 100 g | Surfactant |
| Lecithin | 2 g | Co-surfactant/Complexing Excipient |
| Purified water | 100 g | Co-solvent |

Example 3

Figure 4:
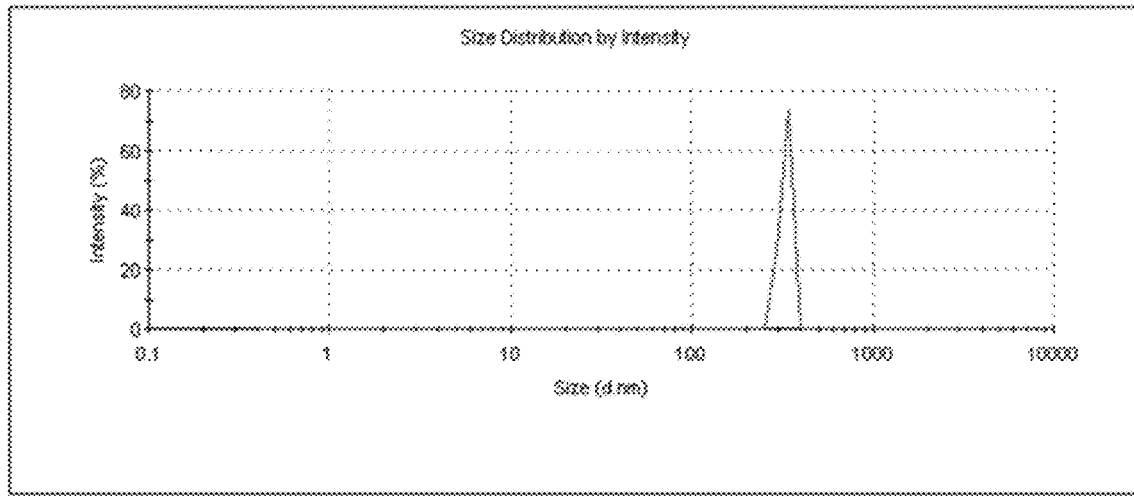
FIG. 4. Particle size distribution of the self-emulsifying formulation from Example 3 (The average particle size=329.9 nm)

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The obtained self-emulsifying preparation was characterized for the particle size by a Malvern dynamic laser diffraction particle size analyzer (FIG. 4).

| Ingredient | Quantity | Function |
|---|---|---|
| Alendronate | 1 g | API |
| PEG 400 | 20 g | Solvent |
| Benzyl alcohol | 17 g | Co-solvent |
| Miglyol 829 | 170 g | Co-solvent |
| Span80 | 25 g | Surfactant |
| Lecithin | 2 g | Co-surfactant/Complexing Excipient |
| Purified water | 100 g | Co-solvent |

Example 4

Figure 5:
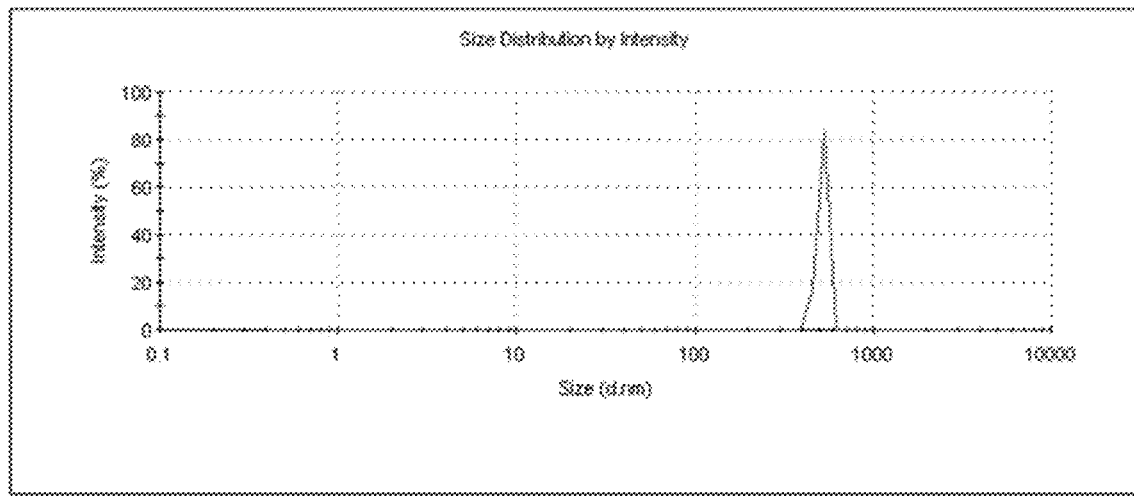
FIG. 5. Particle size distribution of the self-emulsifying formulation from Example 4 (The average particle size=519.5 nm)

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The obtained self-emulsifying preparation was characterized for the particle size by a Malvern dynamic laser diffraction particle size analyzer (FIG. 5).

| Ingredient | Quantity | Function |
|---|---|---|
| Alendronate | 1 g | API |
| Propylene Glycol | 20 g | Solvent |
| Glycerol | 35 g | Co-solvent |
| Miglyol 829 | 70 g | Co-solvent |
| Tween 80 | 35 g | Surfactant |
| Lecithin | 2 g | Co-surfactant/Complexing Excipient |
| Purified water | 200 g | Co-solvent |

Example 5

Figure 6:
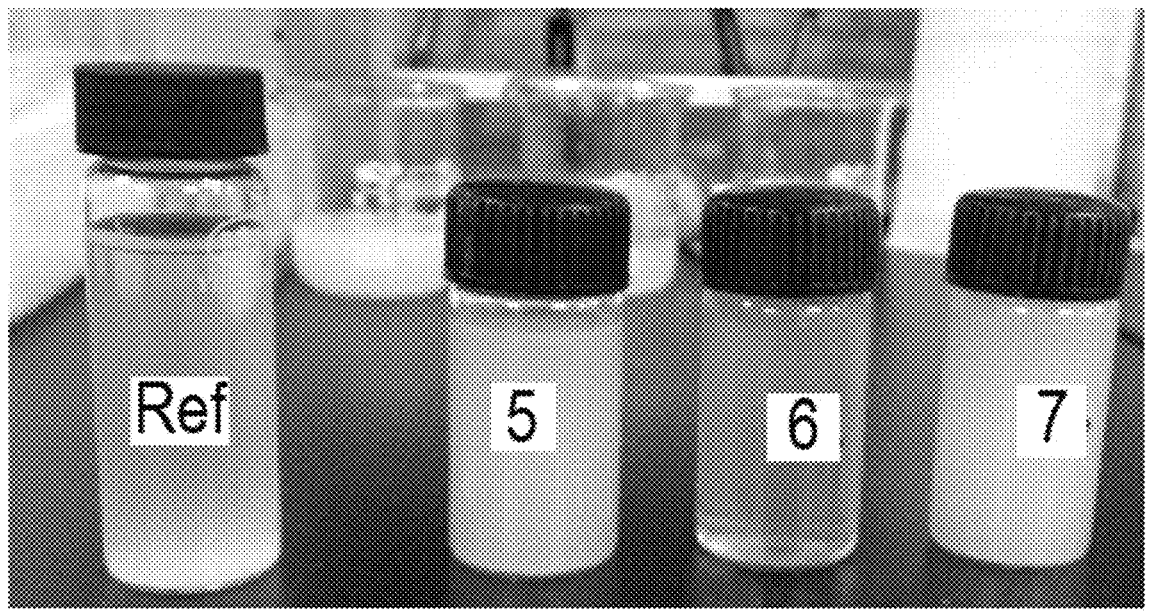
FIG. 6. Self-emulsifying formulation in Example 5, Example 6, Example 7, and Reference sample for turbidity measurement.
Figure 9:
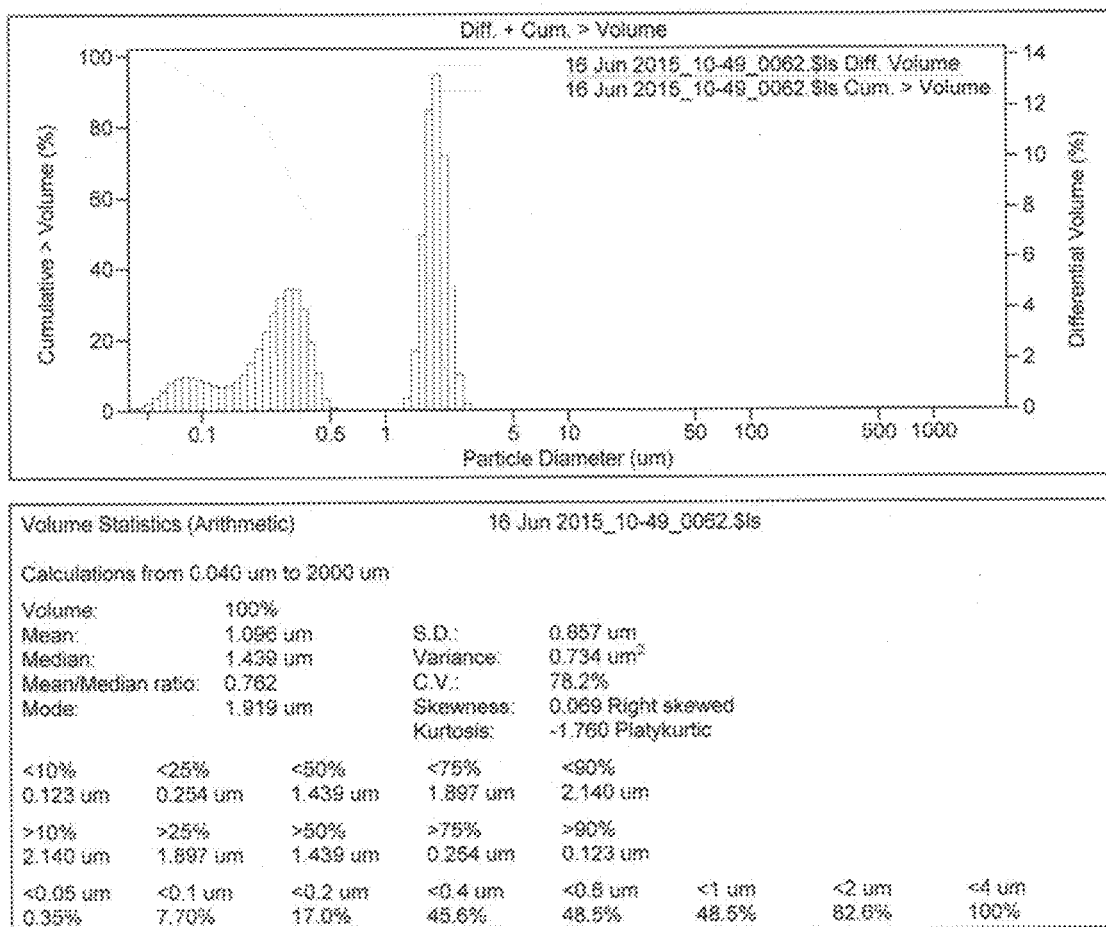
FIG. 9. Particle size distribution of the self-emulsifying formulation from Example 5

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system (FIG. 6). The turbidity of the self-emulsifying formulation was measured by a turbidimeter. The turbidity is 140.8 NTU after 20 times dilution; and 78.3 NTU after 40 times dilution; and 61.2 NTU after 50 times dilution. The obtained self-emulsifying preparation was characterized for the particle size by a Beckman Coulter laser scattering particle size analyzer and the particle size was about 1.096 μm (FIG. 9). The emulsion system was stable at room temperature after three days.

| Ingredient | Quantity | Function |
| --- | --- | --- |
| Risedronate | 1 g | API |
| Labrafac Lipophile WL 1349 | 5 g | Solvent |
| Purified water | 50 g | Co-solvent |
| Transcutol HP | 10 g | Co-solvent |
| Lecithin | 1 g | Surfactant/Complexing Excipient |

Example 6

Figure 10:
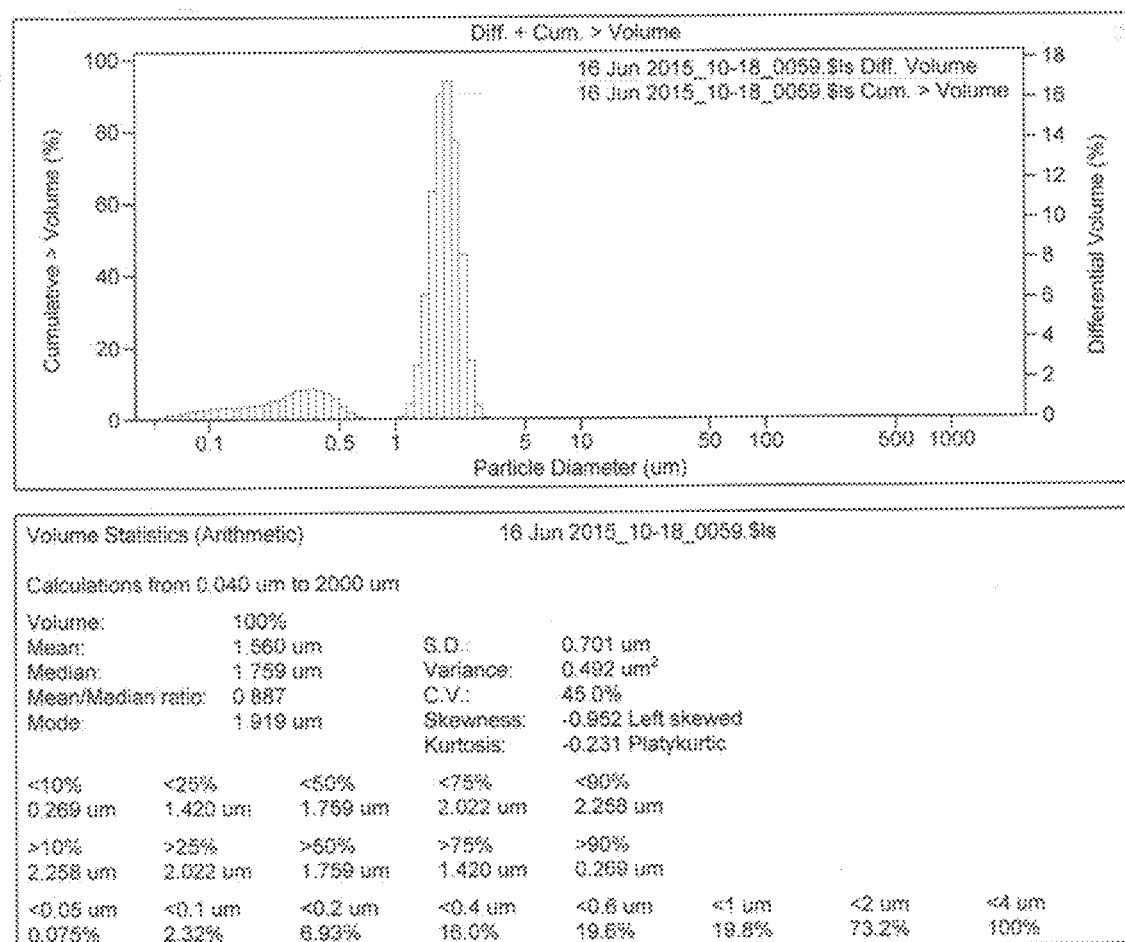
FIG. 10. Particle size distribution of the self-emulsifying formulation from Example 6

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system (FIG. 6). The turbidity of the self-emulsifying formulation was measured by a turbidimeter. The turbidity is 90.8 NTU after 10 times dilution; and 44.8 NTU after 20 times dilution; and 21.9 NTU after 40 times dilution. The obtained self-emulsifying preparation was characterized for the particle size by a Beckman Coulter laser scattering particle size analyzer and the particle size was about 1.560 μm (FIG. 10). The emulsion system was stable at room temperature after three days with slightly reduced turbidity.

| Ingredient | Quantity | Function |
| --- | --- | --- |
| Risedronate | 1 g | API |
| Labrafac Lipophile WL 1349 | 5 g | Solvent |
| Purified water | 50 g | Co-solvent |
| Kolliphor | 10 g | Surfactant |
| Lecithin | 1 g | Co-surfactant/Complexing Excipient |

Example 7

Figure 11:
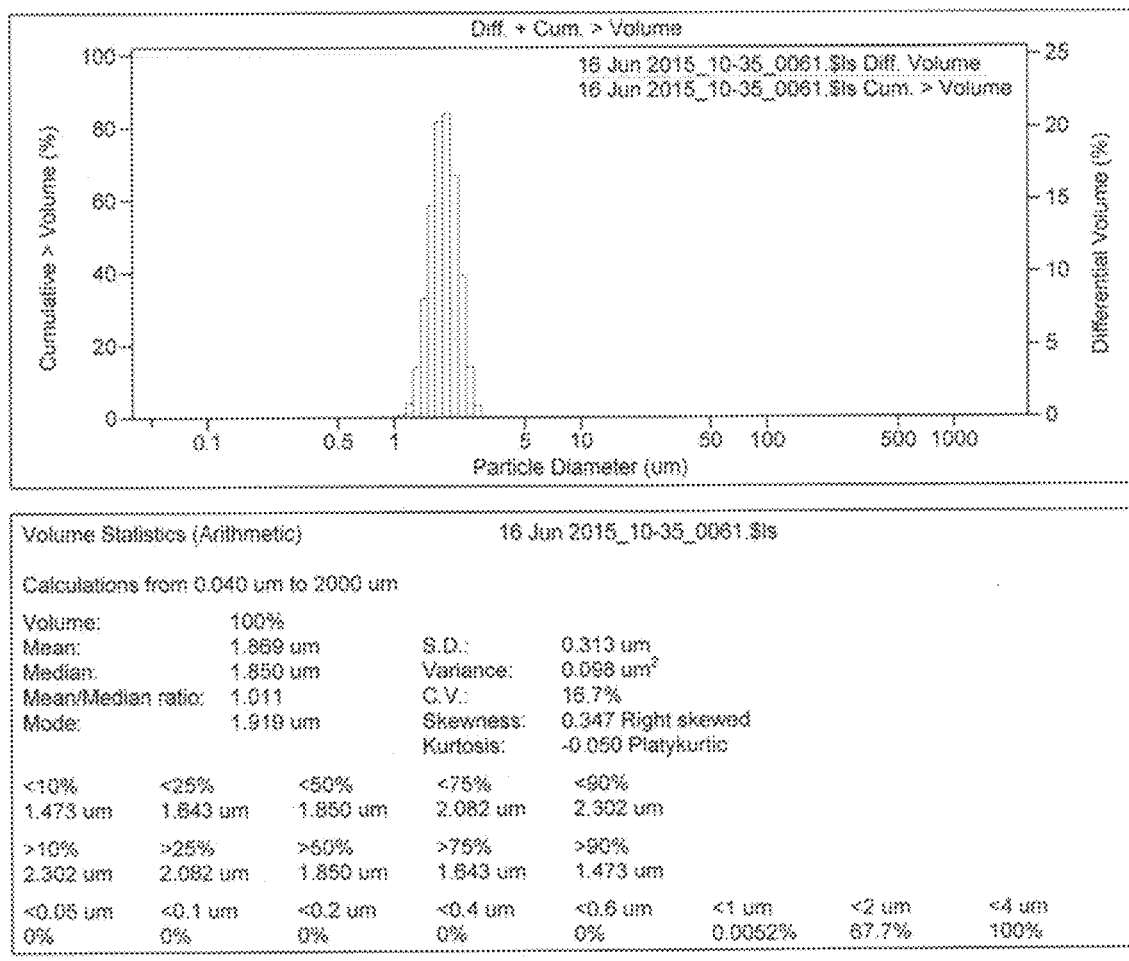
FIG. 11. Particle size distribution of the self-emulsifying formulation from Example 7

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system (FIG. 6). The turbidity of the self-emulsifying formulation was measured by a turbidimeter. The turbidity is 163.6 NTU after 10 times dilution; and 84.8 NTU after 20 times dilution; and 48.4 NTU after 40 times dilution. The obtained self-emulsifying preparation was characterized for the particle size by a Beckman Coulter laser scattering particle size analyzer and the particle size was about 1.096 μm (FIG. 11). The emulsion system was stable at room temperature after three days.

| Ingredient | Quantity | Function |
| --- | --- | --- |
| Risedronate | 1 g | API |
| Labrafac Lipophile WL 1349 | 5 g | Solvent |
| Purified water | 100 g | Co-solvent |
| Labrasol | 10 g | Surfactant |
| Lecithin | 1 g | Co-surfactant/Complexing Excipient |

Example 8

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The liquid was encapsulated into a softgel gelatin capsules according to the skills in art.

| Ingredient | Quantity | Function |
| --- | --- | --- |
| Risedronate | 1 g | API |
| Labrafil M 1944cs | 10 g | Solvent |
| Benzyl alcohol | 25 g | Co-solvent |
| Lecithin | 1 g | Surfactant/Complexing Excipient |
| Ethanol | 50 g | Co-solvent |

Example 9

Figure 7:
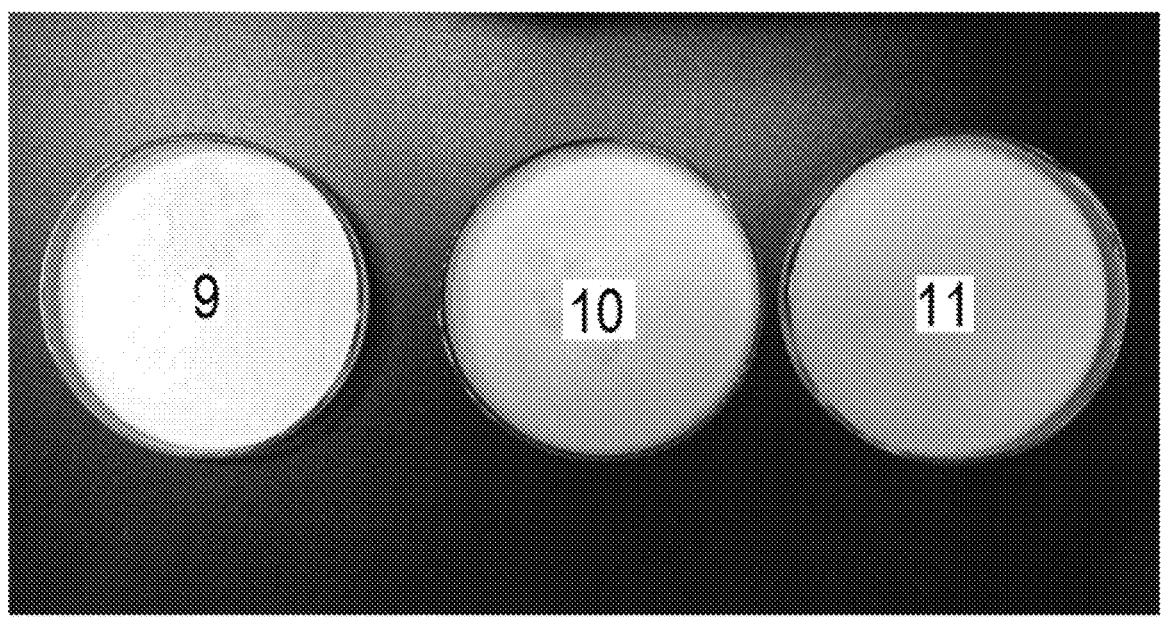
FIG. 7. Solid self-emulsifying formulation after drying in oven in Example 9, Example 10, and Example 11
Figure 8:
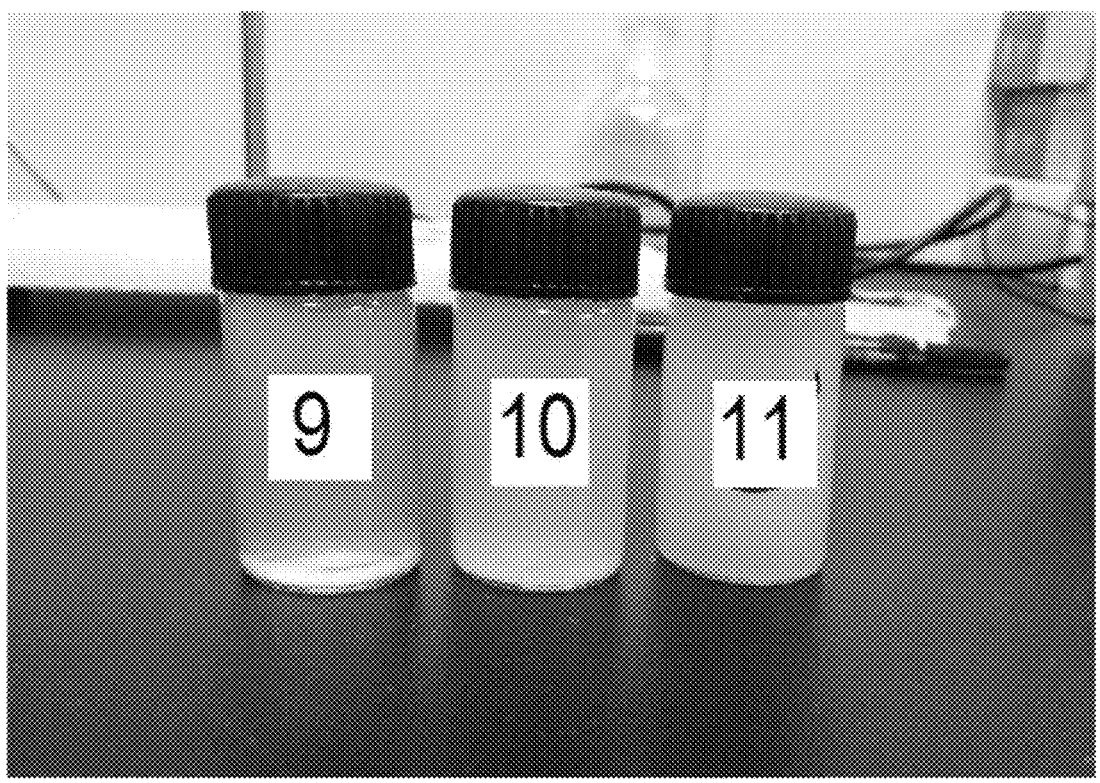
FIG. 8. Re-emulsification of solid self-emulsifying formulation in Example 9, Example 10, and Example 11
Figure 12:
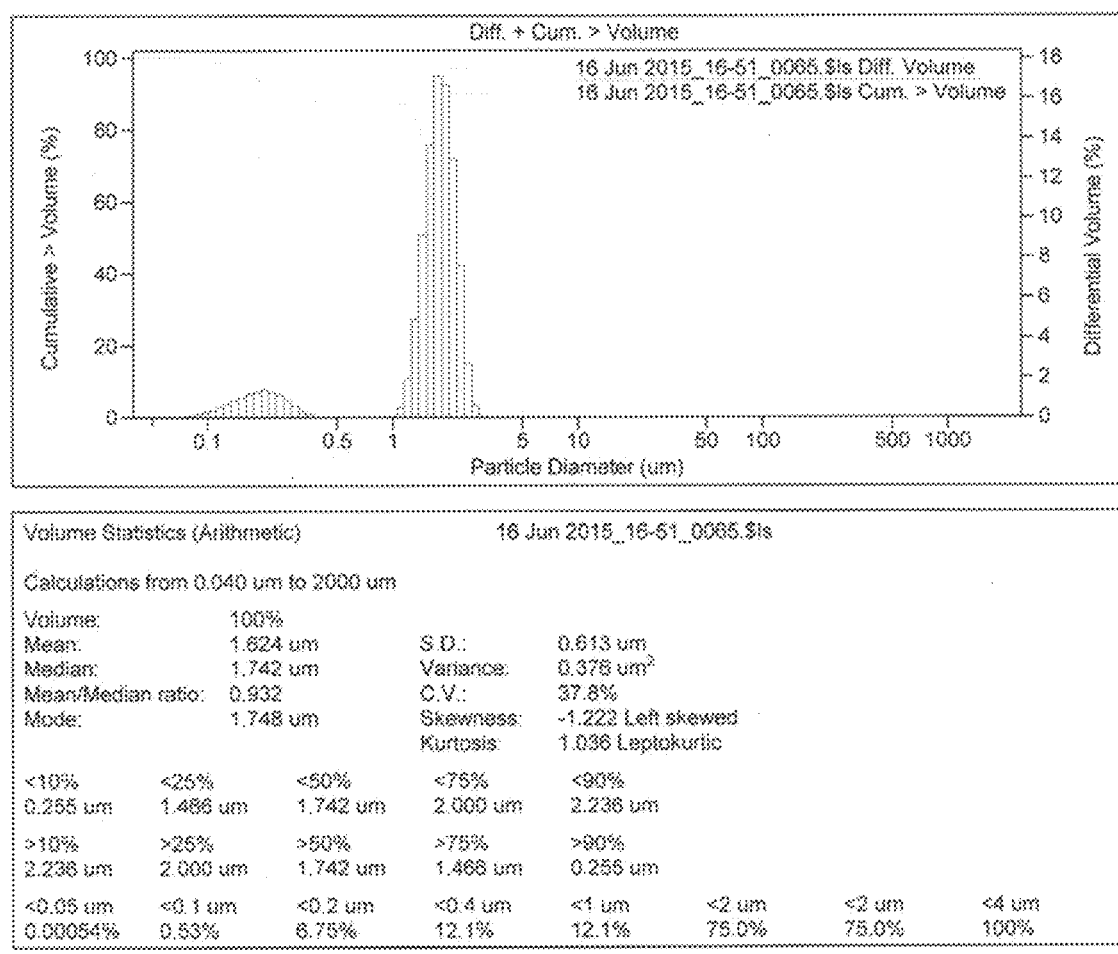
FIG. 12. Particle size distribution of the re-emulsification of solid self-emulsifying formulation from Example 9 (the solidified formulation of Example 5)

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art (FIG. 7). Appropriate amount of solid self-emulsifying system was taken and dissolved in simulated enteric fluid. Solid lactose carrier was dissolved and liquid self-emulsifying system was obtained (FIG. 8). The turbidity of the liquid self-emulsifying formulation was measured by a turbidimeter. The turbidity is 175.6 NTU after 50 times dilution; and 77.8 NTU after 100 times dilution. The obtained self-emulsifying preparation was characterized for the particle size by a Beckman Coulter laser scattering particle size analyzer and the particle size was about 1.869 μm (FIG. 12). The emulsion system was stable at room temperature after three days.

| Ingredient | Quantity | Function |
| --- | --- | --- |
| Risedronate | 1 g | API |
| Labrafac Lipophile WL 1349 | 5 g | Solvent |
| Purified water | 50 g | Co-solvent |
| Transcutol HP | 10 g | Co-solvent |
| Lecithin | 1 g | Surfactant/Complexing Excipient |
| Lactose | 40 g | Carrier |

Example 10

Figure 13:
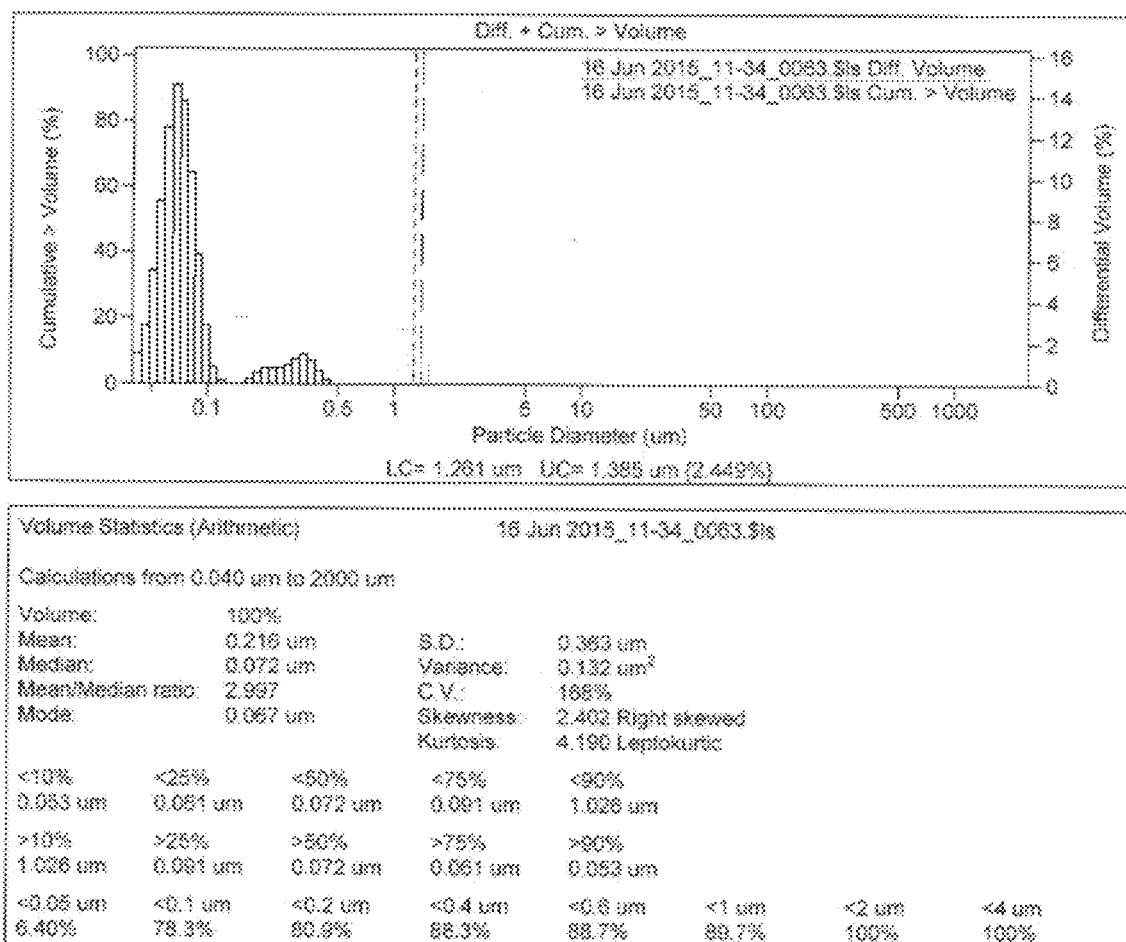
FIG. 13. Particle size distribution of the re-emulsification of solid self-emulsifying formulation from Example 10 (the solidified formulation of Example 6)

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art (FIG. 7). Appropriate amount of solid self-emulsifying system was taken and dissolved in simulated enteric fluid. Solid lactose carrier was dissolved and liquid self-emulsifying system was obtained (FIG. 8). The turbidity of the liquid self-emulsifying formulation was measured by a turbidimeter. The turbidity is 33.3 NTU after 10 times dilution; and 12.6 NTU after 20 times dilution; and 4.6 NTU after 40 times dilution. The obtained self-emulsifying preparation was characterized for the particle size by a Beckman Coulter laser scattering particle size analyzer and the particle size was about 0.216 μm (FIG. 13). The emulsion system was stable at room temperature after three days.

| Ingredient | Quantity | Function |
| --- | --- | --- |
| Risedronate | 1 g | API |
| Labrafac Lipophile WL1349 | 5 g | Solvent |
| Purified water | 20 g | Co-solvent |
| Kolliphor | 10 g | Surfactant |
| Lecithin | 1 g | Co-surfactant/Complexing Excipient |
| Lactose | 40 g | Carrier |

Example 11

Figure 14:
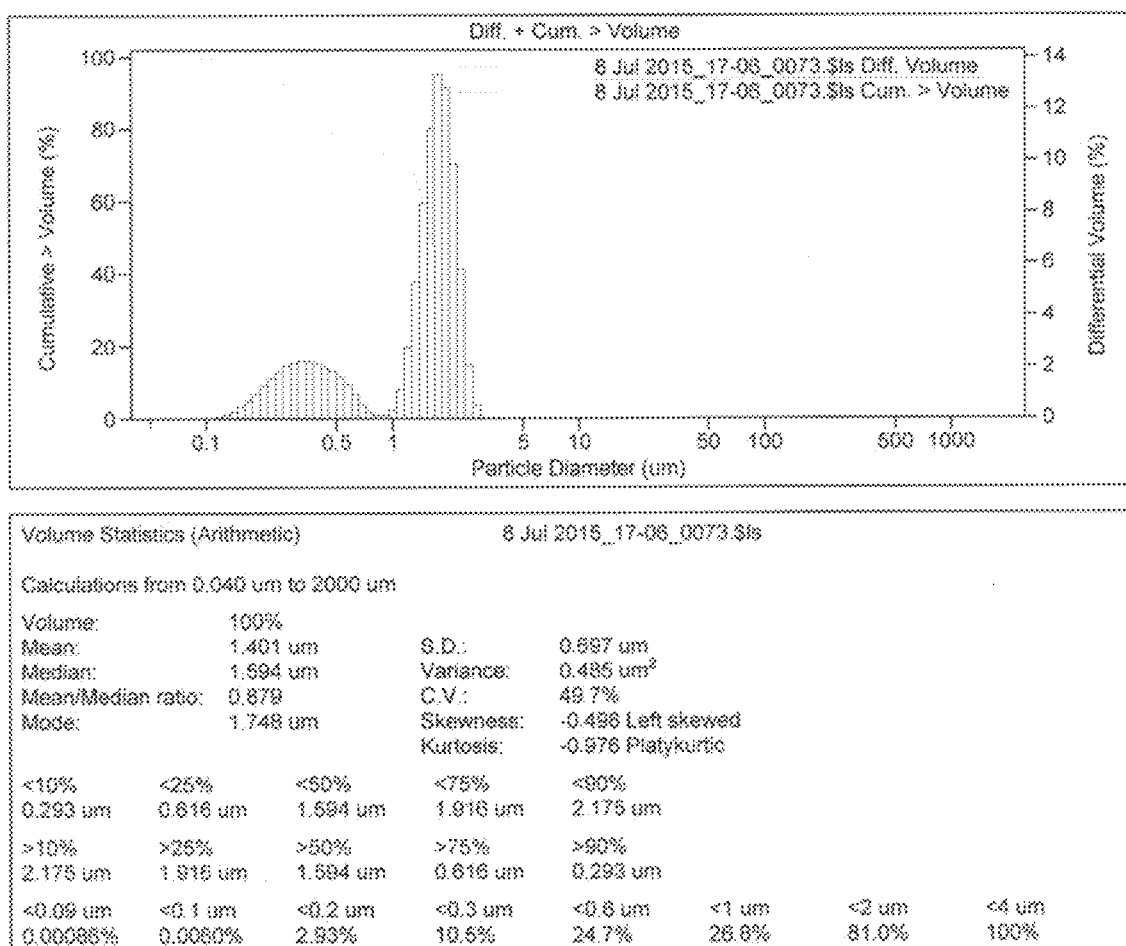
FIG. 14. Particle size distribution of the re-emulsification of solid self-emulsifying formulation from Example 11 (the solidified formulation of Example 7)

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art (FIG. 7). Appropriate amount of solid self-emulsifying system was taken and dissolved in simulated enteric fluid. Solid lactose carrier was dissolved and liquid self-emulsifying system was obtained (FIG. 8). The turbidity of the liquid self-emulsifying formulation was measured by a turbidimeter. The turbidity is 198.3 NTU after 10 times dilution; and 94.3 NTU after 20 times dilution; and 49.6 NTU after 40 times dilution. The obtained self-emulsifying preparation was characterized for the particle size by a Beckman Coulter laser scattering particle size analyzer and the particle size was about 1.401 μm (FIG. 14). The emulsion system was stable at room temperature after three days.

| Ingredient | Quantity | Function |
| --- | --- | --- |
| Risedronate | 1 g | API |
| Labrafac Lipophile WL 1349 | 5 g | Solvent |
| Purified water | 20 g | Co-solvent |
| Labrasol | 10 g | Surfactant |
| Lecithin | 1 g | Co-surfactant/Complexing Excipient |
| Lactose | 40 g | Carrier |

Example 12

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried powder was mixed with diluent and lubricants and compressed into tablets.

| Ingredient | Quantity | Function |
| --- | --- | --- |
| Risedronate | 1 g | API |
| Labrafac Lipophile WL1349 | 5 g | Solvent |
| Purified water | 20 g | Co-solvent |
| Lecithin | 1 g | Surfactant/Complexing Excipient |
| Silica Dioxide | 15 g | Carrier |
| Lactose | 60 g | Carrier |
| Titanium dioxide | 1 g | Carrier |
| Microcrystalline cellulose | 100 g | Diluent |
| Magnesium stearate | 2 g | Glidant |

Example 13

Figure 15:
FIG. 15. Solid self-emulsifying delivery system of bisphosphonates in enteric coated hard gelatin capsules from Example 13

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules (FIG. 15).

Figure 16:
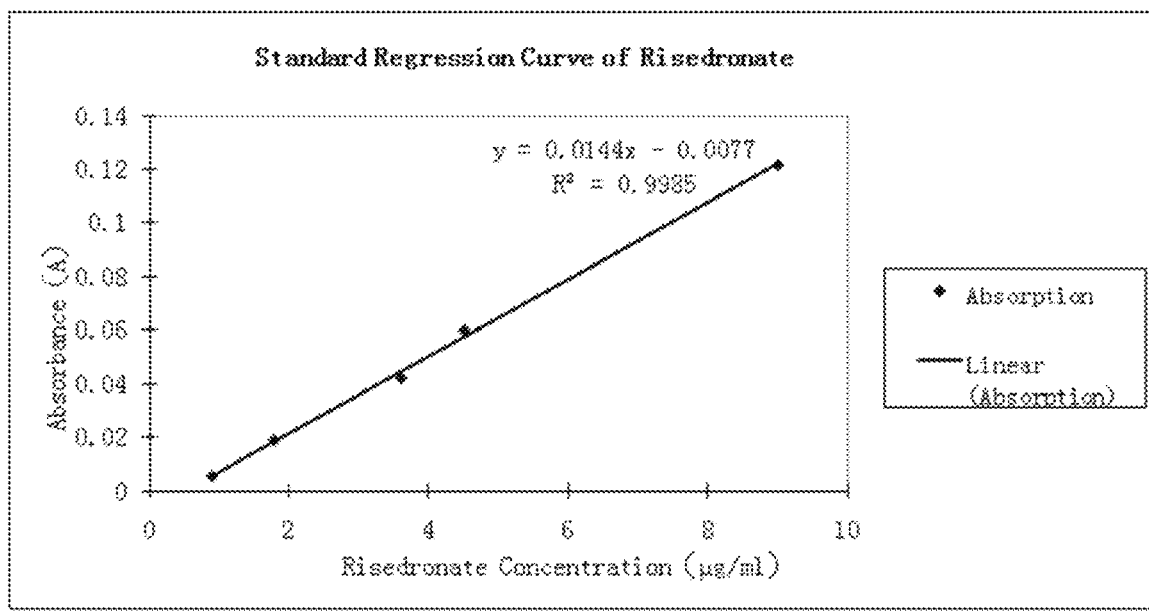
FIG. 16. Standard Regression Curve of Risedronate

The standard curve of working solution of Risedronate was prepared. 9 mg of Risedronate was weighted accurately and dissolved in 100 mL of water. The solution was diluted to a series of solution with following nominal concentrations: 9.0, 4.51, 3.61, 1.80, 0.90 μg/mL. The UV absorption of solutions was measured by a UV spectrometer and the standard regression was determined to be: y=0.0144x−0.007 ($R2=0.9985$) (FIG. 16).

Figure 17:
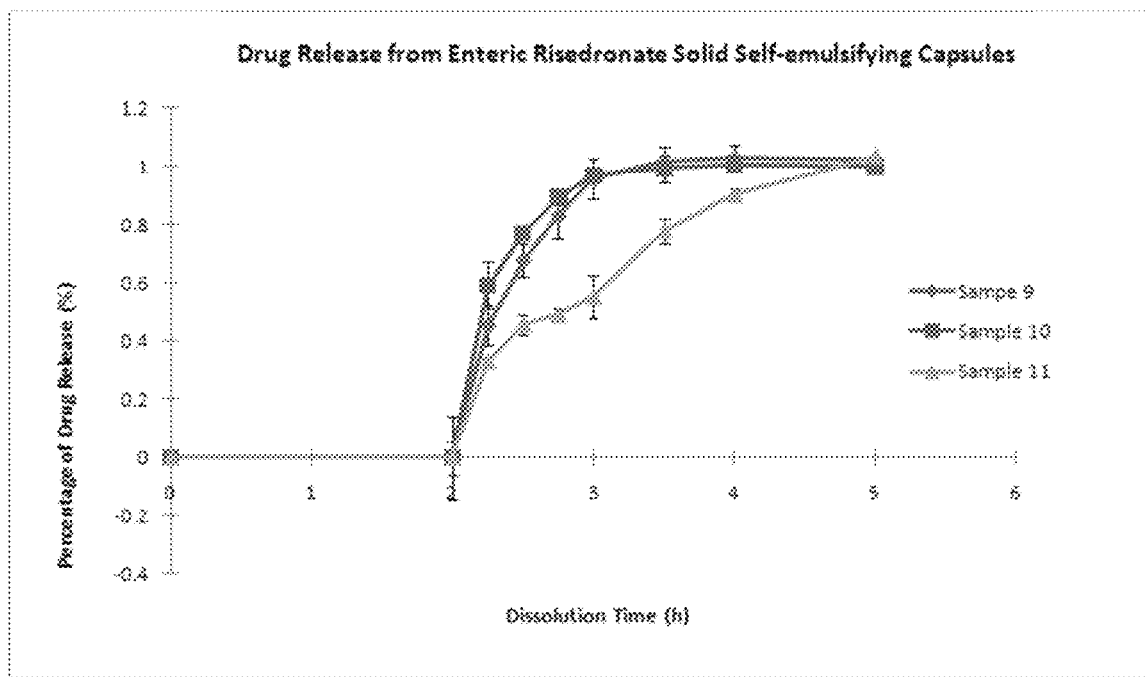
FIG. 17. Delayed drug release from enteric risedronate solid self-emulsifying capsule from Examples 9, 10, 11 (0-120 min in simulated gastric fluid; 120-300 min in simulated small intestinal fluid)

The enteric capsules were subjected to dissolution testing using peddle type dissolution apparatus (0-120 min in simulated gastric fluid; 120-300 min in simulated small intestinal fluid; sampling time: 15, 30, 45, 60, 90, 120, 180 minutes). 15 mL of sample was taken at each time points and equal volume of dissolution medium was added to make up the volume. The absorbance of samples was measured at 262 nm. The enteric capsules of risedronate were prepared using formulae in Examples 9, 10, 11 and drug release study was done with methods described above. From the drug dissolution data (Table 1), the desirable delayed risedronate drug release from enteric solid self-emulsifying capsules was observed as shown in the drug release profile (FIG. 17).

TABLE 1

Drug release from enteric Risedronate self-emulsifying capsules.

| Sample | Time (min) | 0 | 120 | 135 | 150 | 165 | 180 | 210 | 240 | 300 |
|---|---|---|---|---|---|---|---|---|---|---|
| Sample 9 | Drug Release (%) | 0 | 0 | 33.1 | 45.8 | 49.1 | 55.4 | 78.0 | 90.4 | 103.8 |
| | S.D. | 0 | 0 | 2.62% | 1.19% | 3.39% | 2.51% | 7.37% | 4.53% | 2.14% |
| Sample 10 | Drug Release (%) | 0 | 0 | 43.5 | 67.9 | 83.5 | 96.0 | 101.8 | 103.0 | 102.4 |
| | S.D. | 0 | 0 | 14.48% | 6.90% | 5.56% | 8.22% | 6.79% | 4.92% | 4.25% |
| Sample 11 | Drug Release (%) | 0 | 0 | 59.2 | 77.2 | 89.3 | 97.2 | 99.5 | 100.9 | 100.2 |
| | S.D. | 0 | 0 | 5.72% | 8.03% | 0.66% | 1.51% | 1.93% | 4.47% | 2.22% |

Example 14

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules.

| Ingredient | Quantity | Function |
|---|---|---|
| Risedronate | 1 g | API |
| Vitamin D | 3.1 mg | API |
| Labrafac Lipophile WL1349 | 5 g | Solvent |
| Purified water | 20 g | Co-solvent |
| Kolliphor | 10 g | Surfactant |
| Lecithin | 1 g | Co-surfactant/Complexing Excipient |
| Lactose | 40 g | Carrier |

Example 15

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules.

| Ingredient | Quantity | Function |
|---|---|---|
| Risedronate | 1 g | API |
| Vitamin D | 3.1 mg | API |
| Labrafac Lipophile WL1349 | 5 g | Solvent |
| Purified water | 20 g | Co-solvent |
| Transcutol HP | 10 g | Co-solvent |
| Lecithin | 1 g | Co-surfactant/Complexing Excipient |
| Lactose | 40 g | Carrier |

Example 16

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules.

| Ingredient | Quantity | Function |
|---|---|---|
| Risedronate | 1 g | API |
| Labrafac Lipophile WL1349 | 5 g | Solvent |
| Purified water | 20 g | Co-solvent |
| Kolliphor | 10 g | Surfactant |
| DOTAP | 1 g | Complexing Excipient |
| Lactose | 40 g | Carrier |

Example 17

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules.

| Ingredient | Quantity | Function |
|---|---|---|
| Risedronate | 1 g | API |
| Labrafac Lipophile WL1349 | 5 g | Solvent |
| Purified water | 20 g | Co-solvent |
| Kolliphor | 10 g | Surfactant |
| Hydrogenated Palm Trimethylammonium chloride | 1 g | Complexing Excipient |
| Lactose | 40 g | Carrier |

Example 18

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules.

| Ingredient | Quantity | Function |
| --- | --- | --- |
| Risedronate | 1 g | API |
| Labrafac Lipophile WL1349 | 5 g | Solvent |
| Purified water | 20 g | Co-solvent |
| Kolliphor | 10 g | Surfactant |
| Dimethyldioctadecylammonium chloride | 1 g | Complexing Excipient |
| Lactose | 40 g | Carrier |

Example 19

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules.

| Ingredient | Quantity | Function |
| --- | --- | --- |
| Risedronate | 1 g | API |
| Labrafac Lipophile WL1349 | 5 g | Solvent |
| Purified water | 20 g | Co-solvent |
| Kolliphor | 10 g | Surfactant |
| N-acetylated chitosan | 1 g | Complexing Excipient |
| Lactose | 40 g | Carrier |

Example 20

A self-emulsifying formulation of bisphosphonate was prepared using standard techniques known to those skilled in art. Bisphosphonate was weighed and mixed with solvent, co-solvent, surfactant, and co-surfactant/complexing excipient and thereafter obtained a self-emulsifying drug delivery system. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules.

| Ingredient | Quantity | Function |
| --- | --- | --- |
| Risedronate | 1 g | API |
| Labrafac Lipophile WL1349 | 5 g | Solvent |
| Purified water | 20 g | Co-solvent |
| Kolliphor | 10 g | Surfactant |
| Dextran-spermine | 1 g | Complexing Excipient |
| Lactose | 40 g | Carrier |

Example 21

An over-saturated self-emulsifying formulation of bisphosphonate was prepared using standard techniques known to those skilled in art. Bisphosphonate was weighed and mixed with solvent, co-solvent, surfactant, and co-surfactant/complexing excipient, crystallization inhibitors of over-saturated solution, and thereafter obtained an over-saturated self-emulsifying drug delivery system after heating and cooling cycles. The system was further mixed with solid carriers and mixed well so liquid was fully absorbed by solid carrier powder. The mixture was dried in the oven or freeze dried according to the skills known in art. The dried mixture powder was filled into an enteric coated hard gelatin capsules.

| Ingredient | Quantity | Function |
| --- | --- | --- |
| Risedronate | 3 g | API |
| Labrafac Lipophile WL1349 | 5 g | Solvent |
| Purified water | 20 g | Co-solvent |
| Kolliphor | 10 g | Surfactant |
| Lecithin | 3 g | Co-surfactant/Complexing Excipient |
| HPMC | 3 g | Crystallization Inhibitor |

We claim:

1. A self-emulsifying pharmaceutical formulation comprising:
    an active agent having a negative charge, the active agent being a bisphosphonic acid, a bisphosphonate, or a combination thereof;
    one or more complexing excipients having at least one positive charge and being selected from the group consisting of lecithin, dimethyldioctadecylammonium, dioleoyl-3-trimethylammonium propane (DOTAP), hydrogenated palm trimethylammonium, dextran-spermine, N-acetylated chitosan and combinations thereof, wherein the active agent and the one or more complexing excipients form a complex through ionic interaction; and
    one or more surfactants having an HLB value of 10 or greater, selected from the group consisting of polyethylene glycol fatty acid esters, alcohol-oil transesterification products, polyglycerized fatty acids, propylene glycol fatty acid esters, mixtures of propylene glycol fatty acid esters and glycerol fatty acid esters, mono- and diglycerides, sterol and sterol derivatives, sorbitan fatty acid esters and polyethylene glycol sorbitan fatty acid esters, sugar esters, polyethylene glycol alkyl ethers and polyethylene glycol alkyl phenol ethers, polyoxyethylene-polyoxypropylene block copolymers, lower alcohol fatty acid esters, ionic surfactants and ionizable surfactants
    wherein, relative to a total weight of the self-emulsifying pharmaceutical formulation the active agent is in an amount of 0.1-20% and the one or more complexing excipients are in an amount of 0.1-40%.

2. The self-emulsifying pharmaceutical formulation of claim 1, wherein the active agent is 1-hydroxyethane-1,1-diphosphonic acid (etidronic acid), 1,1-dichloromethylene-1,1-bisphosphonic acid (clodronic acid), 3-amino-1-hydroxypropylidene-1,1-bisphosphonic acid (pamidronic acid), 4-amino-1-hydroxybutylidene-1,1-bisphosphonic acid (alendronic acid), 6-amino-1-hydroxy-hexylidene-1,1-bisphosphonic acid (neridronic acid), (4-chlorophenyl)-thiomethane-1,1-diphosphonic acid (tiludronic acid), 2-(3-pyridinyl)-1-hydroxy-2-(3-pyridinyl)-ethylidene-1,1-bisphosphonic acid (risedronic acid), cycloheptylaminomethylene-1,1-bisphosphonic acid (cimadronic acid), 1-hydroxy-3-(N-methyl-N-pentylamino)-propylidene-1,1-bisphosphonic acid (ibandronic acid), 3-(dimethylamino)-1-hydroxypropylidene-1,1-bisphosphonic acid (olpadronic acid), [2-(2-pyridinyl)-ethylidene]-1,1-bisphosphonic acid (piridronic acid), 1-hydroxy-2-(1H-imidazol-1-yl)ethylidene-1,1-bisphosphonic acid (zoledronic acid) or a pharmaceutically acceptable salt thereof.

3. The self-emulsifying pharmaceutical formulation of claim 1 wherein ionizable surfactants are selected from the group consisting of phospholipids, chitosan or derivatives thereof, long carbon chain tertiary or quaternary ammoniums, and cyclodextrins or derivatives thereof.

4. The self-emulsifying pharmaceutical formulation of claim 1 further comprising one or more solvents selected from the group consisting of alcohols, polyols, ethers, amides, esters, polyethylene glycols, oils, triglycerides, water, and mixtures thereof.

5. The self-emulsifying pharmaceutical formulation of claim 1, further comprising a solid carrier selected from the group consisting of dibasic calcium phosphonate, magnesium aluminometasilicate, lactose, a cellulose derivative, magnesium stearate, croscarmellose sodium, silica dioxide, calcium carbonate, starch, resin, maltodextrin, cyclodextrin, dextran, silicate, zinc dioxide, titanium dioxide, and mixtures thereof.

6. The self-emulsifying pharmaceutical formulation of claim 1, further comprising one or more crystallization inhibitors for improving the stability of an over-saturated self-emulsifying formulation.

7. The self-emulsifying pharmaceutical formulation of claim 6 wherein the crystallization inhibitor includes HPMC.

8. The self-emulsifying pharmaceutical formulation of claim 1, further comprising one or more pharmaceutically acceptable excipients selected from the group consisting of buffering agents, pH adjusters, antioxidants, preservatives, chelating agents, viscomodulators, tonicifiers, flavorants, colorants, odorants, opacifiers, suspending agents, antifoaming agents, binders, fillers, plasticizers, lubricants, and mixtures thereof.

9. An oral dosage form comprising the self-emulsifying pharmaceutical formulation of claim 1.

10. The oral dosage form of claim 9 wherein the self-emulsifying pharmaceutical formulation comprises a solid carrier and the oral dosage form is a solid dosage form.

11. The oral dosage form of claim 9 wherein the self-emulsifying pharmaceutical formulation is liquid that is encapsulated in capsules.

12. The self-emulsifying pharmaceutical formulation of claim 5 wherein the cellulose derivative is methyl cellulose or hydroxypropyl methylcellulose (HPMC).

13. A method for treating a patient having a disorder, condition or disease involving calcium or phosphate metabolism, the method comprising administering to the patient a therapeutically effective amount of the self-emulsifying pharmaceutical formulation of claim 1.

14. The method claim 13 wherein the patient to be treated has osteoporosis, Paget's disease, periprosthetic bone loss or osteolysis, metastatic bone disease, hypercalcemia of malignancy, multiple myeloma, periodontal disease, or tooth loss.

* * * * *